United States Patent
Amajjahe et al.

(10) Patent No.: US 11,865,374 B2
(45) Date of Patent: Jan. 9, 2024

(54) FUNCTIONALIZED POLYMERS

(71) Applicants: Evonik Operations GmbH, Essen (DE); Evonik Corporation, Piscataway, NJ (US)

(72) Inventors: Sadik Amajjahe, Düsseldorf (DE); Matthias Mentel, Dortmund (DE); Juergen Meyer, Essen (DE); Andrew Wilson Wang, Macungie, PA (US); Arnoldo Fonseca, Harleysville, PA (US)

(73) Assignees: Evonik Operations GmbH, Essen (DE); Evonik Corporation, Piscataway, NJ (US)

( * ) Notice: Subject to any disclaimer, the term of this patent is extended or adjusted under 35 U.S.C. 154(b) by 339 days.

(21) Appl. No.: 16/763,009

(22) PCT Filed: Nov. 2, 2018

(86) PCT No.: PCT/EP2018/080003
§ 371 (c)(1),
(2) Date: May 11, 2020

(87) PCT Pub. No.: WO2019/096593
PCT Pub. Date: May 23, 2019

(65) Prior Publication Data
US 2020/0383896 A1    Dec. 10, 2020

Related U.S. Application Data

(60) Provisional application No. 62/586,266, filed on Nov. 15, 2017.

(51) Int. Cl.
| | | |
|---|---|---|
| *A61K 38/00* | (2006.01) | |
| *A61Q 5/00* | (2006.01) | |
| *C08F 220/18* | (2006.01) | |
| *A61K 8/81* | (2006.01) | |
| *A61Q 1/02* | (2006.01) | |
| *A61Q 1/06* | (2006.01) | |
| *A61Q 9/02* | (2006.01) | |
| *A61Q 15/00* | (2006.01) | |
| *A61Q 17/04* | (2006.01) | |
| *A61Q 19/00* | (2006.01) | |
| *A61Q 19/08* | (2006.01) | |

(52) U.S. Cl.
CPC .............. *A61Q 5/00* (2013.01); *A61K 8/8152* (2013.01); *A61Q 1/02* (2013.01); *A61Q 1/06* (2013.01); *A61Q 9/02* (2013.01); *A61Q 15/00* (2013.01); *A61Q 17/04* (2013.01); *A61Q 19/002* (2013.01); *A61Q 19/004* (2013.01); *A61Q 19/007* (2013.01); *A61Q 19/08* (2013.01); *C08F 220/1818* (2020.02)

(58) Field of Classification Search
CPC .... A61K 2800/10; A61K 8/8152; A61Q 1/02; A61Q 1/06; A61Q 15/00; A61Q 17/04; A61Q 19/00; A61Q 19/002; A61Q 19/004; A61Q 19/007; A61Q 19/04; A61Q 19/08; A61Q 5/00; A61Q 9/02; C08F 220/1818; C08F 220/20; C08F 220/18

See application file for complete search history.

(56) References Cited

U.S. PATENT DOCUMENTS

| | | | |
|---|---|---|---|
| 4,128,635 A * | 12/1978 | Hase | A61K 8/8158 514/772.4 |
| 8,653,214 B2 | 2/2014 | Venzmer et al. | |
| 9,776,951 B2 | 10/2017 | Friedrich et al. | |
| 10,292,925 B2 | 5/2019 | Gu et al. | |
| 10,407,592 B2 | 9/2019 | Amajjahe et al. | |
| 2007/0166250 A1* | 7/2007 | Hiwatashi | C08F 293/00 424/61 |
| 2013/0310530 A1 | 11/2013 | Jha et al. | |
| 2015/0210795 A1 | 7/2015 | Jhaveri | |
| 2015/0299520 A1 | 10/2015 | Mansei et al. | |
| 2016/0213600 A1 | 7/2016 | Klostermann et al. | |
| 2016/0250137 A1 | 9/2016 | Noor et al. | |
| 2017/0202770 A1 | 7/2017 | Friedrich et al. | |
| 2018/0258228 A1 | 9/2018 | Amajjahe et al. | |
| 2019/0202771 A1 | 7/2019 | von Hof et al. | |
| 2019/0330407 A1 | 10/2019 | Amajjahe et al. | |

FOREIGN PATENT DOCUMENTS

| | | |
|---|---|---|
| CN | 105694773 A | 6/2016 |
| EP | 0 569 639 A1 | 11/1993 |
| EP | 3047845 A1 | 7/2016 |
| WO | 2013/148614 A2 | 10/2013 |
| WO | 2014/118370 A1 | 8/2014 |

OTHER PUBLICATIONS

Hartung et al., U.S. Appl. No. 16/636,678, filed Feb. 5, 2020.
International Search Report dated Jan. 21, 2019 in PCT/EP2018/080003 (5 pages).
Written Opinion dated Jan. 21, 2019 in PCT/EP2018/080003 (8 pages).
Molar mass distribution—Wikipedia, last edited on Feb. 14, 2023, pp. 1-4.

* cited by examiner

*Primary Examiner* — Aradhana Sasan
*Assistant Examiner* — Mercy H Sabila
(74) *Attorney, Agent, or Firm* — Grüneberg and Myers, PLLC

(57) ABSTRACT

The invention relates to functionalized polymers, a process for producing functionalized polymers and the use of functionalized polymers, especially in the field of personal care.

19 Claims, No Drawings

FUNCTIONALIZED POLYMERS

CROSS REFERENCE TO RELATED APPLICATIONS

This application is a 35 U.S.C. § 371 U.S. national phase entry of International Application No. PCT/EP2018/080003 having an international filing date of Nov. 2, 2018, which claims the benefit of U.S. Provisional Application No. 62/586,266 filed Nov. 15, 2017, each of which is incorporated herein by reference in its entirety.

FIELD

The invention relates to functionalized polymers, a process for producing functionalized polymers and the use of functionalized polymers, especially in the field of personal care.

BACKGROUND

US2016250137 discloses personal care compositions comprising an oil in water emulsion, at least one C12-C22 side chain crystalline polymer which contains at least one hydroxyl functional group wherein the side chain crystalline polymer has a crystalline melting point from 40 to 70° C.; and,
at least one active compound that interacts with skin wherein the active compound is incorporated into a crystalline matrix of the side chain crystalline polymer and wherein the active ingredient is released from the crystalline matrix at body temperatures, wherein the personal care composition is devoid of sunscreen actives.

SUMMARY

It is an object of the invention to provide for functionalized polymers with supreme properties in personal care applications.

DETAILED DESCRIPTION

It was found that, surprisingly, that the polymers according to claim 1 bear supreme properties in personal care applications.

The present invention therefore provides special polymers, that are characterized in, that the polymer has a number average molecular weight $M_n$ in the range of from 2,000 to 9,000 g/mol.

The invention further provides a process for producing polymers as well as personal care formulations containing certain polymers.

An advantage of the current invention is, that the polymers lead to a more pleasant skin feel.

Another advantage of the current invention is, that the polymers achieve high water resistance of sunscreen formulations.

A further advantage of the current invention is, that the polymers offer an outstanding compatibility with organic UV-filters.

A further advantage of the current invention is, that the polymers are easier to formulate.

A further advantage of the current invention is, that the polymers achieve a good dispersion of pigments.

Further, the current invention leads to a higher ability of fragrance retention on hair from personal care formulations.

The polymers of the present invention, the process of the present invention, the preparations obtainable with these and their use will now be described by way of example without any intention to restrict the invention to these exemplary embodiments. Where ranges, general formulae or classes of compounds are recited herein below, these shall encompass not just the corresponding ranges or groups of compounds explicitly mentioned, but also all sub-ranges and sub-groups of compounds obtainable by removing individual values (ranges) or compounds.

When documents are cited in the context of the present description, their contents shall fully form part of the disclosure content of the present invention.

"natural numbers" as used in the present invention do not encompass 0 (zero).

Unless stated otherwise, all percentages (%) given are percentages by weight.

Unless stated otherwise, all ppm given are ppm by weight.

Viscosity values recited in the context of this invention are to be understood as meaning, unless otherwise stated, dynamic viscosities which can be determined using methods familiar to a person skilled in the art. Measurements recited herein below were determined at a pressure of 101325 Pa and a temperature of 23° C., unless otherwise stated.

Claimed is a polymer comprising monomeric units of general formula (I)

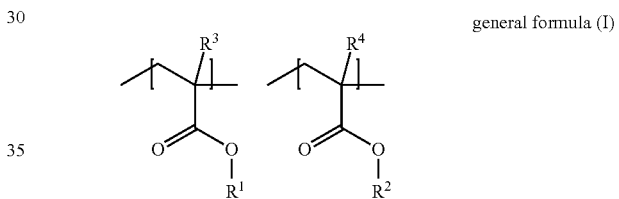

general formula (I)

with
$R^1$=independently from each other selected from the group consisting of alkyl radicals and alkenyl radicals, which both may be branched or straight chained, unsubstituted or substituted, especially substituted by hydroxyl-groups,
$R^2$=independently from each other selected from the group consisting of hydroxyl substituted hydrocarbyl radicals, preferably alkyl radicals, with 1 to 10, preferably 2 to 6, more preferably 2 to 4, carbon atoms, and
$R^3$ and $R^4$=independently from each other selected from the group consisting of H and methyl, preferably H,
with the monomeric units of general formula (I) making up for at least 90 wt.-%, preferably 95 wt.-%, of the total weight of the polymer,
with at least 90 wt.-% of all $R^1$ are selected from the group of alkyl and alkenyl radicals with 6 to 32, preferably 10 to 26, more preferably 12 to 22, carbon atoms, with the wt.-% referring to the sum of all $R^1$ present in the polymer, and
with the weight ratio of the sum of all $R^2$-bearing-units to the sum of all $R^1$-bearing-units being in the range of 1:100 to 1:0.5, preferably 1:60 to 1:0.8, more preferably 1:30 to 1:1, characterized in, that the polymer has a number average molecular weight $M_n$ in the range of from 2,000 to 9,000, preferably 5,000 to 8500, more preferably 6,000 to 8,000, g/mol.

It is obvious by the above that $R^1$ in the context of the present invention does not encompass the groups defined by $R^2$.

The polymers according to the invention are copolymers, including random copolymers, graft copolymers and block copolymers.

Preferably the polymer according to the present invention consists of monomeric units of general formula (I)

The at least 90 wt.-% of all $R^1$ can be mixtures, of course, and it is preferred, that the at least 90 wt. % of all $R^1$ contain a mixture of 0 wt.-%-5 wt.-% cetyl, 40 wt.-%-55 wt. % stearyl, 1 wt.-%-15 wt.-% arachidyl, 35 wt. %-45 wt.-% behenyl and 0 wt.-% to 5 wt.-% lignoceryl, the wt.-% referring to the sum of all $R^1$ present in the polymer.

It is alternatively preferred, that the at least 90 wt.-% of all $R^1$ contain a mixture of 0 wt.-%-3 wt.-% myristyl, 40 wt.-%-50 wt.-% cetyl, 40 wt.-%-50 wt.-% stearyl and 0 wt.-%-1 wt.-% arachidyl, the wt.-% referring to the sum of all $R^1$ present in the polymer.

The at least 90 wt.-% of all $R^1$ preferably are selected from the group of linear alkyl and alkenyl radicals 12 to 22 carbon atoms, with stearyl and behenyl especially preferred.

$R^2$ independently from each other preferably are selected from the group consisting of 2-hydroxy-ethyl, 2-hydroxy-propyl, 2-hydroxy-1-methylethyl, 4-hydroxy-butyl, 2-hydroxy-3-phenoxypropyl and 2,3-dihydroxypropyl, with 2-hydroxy-ethyl being especially preferred.

Preferably, the polymer according to instant invention is characterized in, that the polymer has a melting point in the range of 41° C. to 69° C., preferably 44° C. to 68° C., more preferably 62° C. to 67° C.

Preferably, the polymer according to instant invention is characterized in, that the polymer has a weight average molecular weight $M_w$ in the range of from 10,000 to 500,000, preferably 12,000 to 250,000, more preferably 15,000 to 150,000, g/mol.

Preferably, the polymer according to instant invention is characterized in, that the polymer has a ratio of weight average molecular weight $M_w$ to number average molecular weight $M_n$ in the range of from 0.1 to 3.6, preferably 0.5 to 3.5, more preferably 2.3 to 3.3.

Alternatively preferred, the polymer according to instant invention is characterized in, that the polymer has a ratio of weight average molecular weight $M_w$ to number average molecular weight $M_n$ in the range of from 8 to 100, preferably 10 to 80, more preferably 12 to 50.

Preferably, the polymer according to instant invention is characterized in, that $R^1$=independently from each other selected from the group consisting of stearyl and behenyl, $R^2$=selected from the group consisting of 2-hydroxy-ethyl, 2-hydroxy-propyl, 2-hydroxy-1-methylethyl, 4-hydroxy-butyl, 2-hydroxy-3-phenoxypropyl and 2,3-dihydroxypropyl, with 2-hydroxy-ethyl being especially preferred, $R^3$ and $R^4$=H.

The polymers of the present invention are obtainable in various ways. The polymers of the present invention are preferably obtained by the herein below described process of the present invention. Therefore, a process for preparing a polymer is claimed comprising the steps of A) providing a monomer (1) of general formula (II) and a monomer (2) of general formula (III)

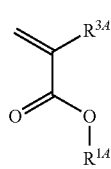

general formula (II)

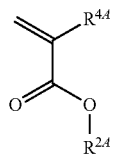

general formula (III)

-continued with $R^{1,4}$=independently from each other selected from the group consisting of alkyl radicals and alkenyl radicals, which both may be branched or straight chained, unsubstituted or substituted, especially substituted by hydroxyl-groups, $R^{2,4}$=independently from each other selected from the group consisting of hydroxyl substituted hydrocarbyl radicals, preferably alkyl radicals, with 1 to 10, preferably 2 to 6, more preferably 2 to 4, carbon atoms, $R^{3,4}$ and $R^{4,4}$=independently from each other selected from the group consisting of H and methyl, preferably H, and with at least 90 wt.-% of all $R^{1,4}$ are selected from the group of alkyl and alkenyl radicals with 6 to 32, preferably 10 to 26, more preferably 12 to 22, carbon atoms, with the wt.-% referring to the sum of all $R^{1,4}$ present in the polymer, and a weight ratio of monomer (1) to monomer (2) in the range of 1:100 to 1:0.5, preferably 1:60 to 1:0.8, more preferably 1:30 to 1:1, B) addition of at least one initiator to polymerize the monomers and performing a radical polymerisation, optionally C) removal of excess of monomers, and, optionally, D) purification of the obtained polymer, characterized in, that the at least one initiator is added in an amount of from 5 to 20,000 ppm, preferably from 50 to 10000 ppm, more preferably 100 to 5000 ppm, wherein the ppm refer to the total weight of the sum of all monomers (1) and (2) provided in process step A).

It is obvious by the above that $R^{1,4}$ in the context of the present invention does not encompass the groups defined by $R^{2,4}$.

$R^{1,4}$ preferably is independently from each other selected from the group consisting of unsubstituted alkyl radicals and alkenyl radicals.

$R^{2,4}$ independently from each other preferably are selected from the group consisting of 2-hydroxy-ethyl, 2-hydroxy-propyl, 2-hydroxy-1-methylethyl, 4-hydroxy-butyl, 2-hydroxy-3-phenoxypropyl and 2,3-dihydroxypropyl, with 2-hydroxy-ethyl being especially preferred The initiator added in process step B) according to the instant invention is an initiator, which can be solid, liquid or dissolved in solvent.

The initiator added in process step B) according to the instant invention is preferably selected from the group of 2,2'-azo-bis(2-methyl propionitrile), 2,2'-azodi(2-methylbutyronitrile), 1,1'-azodi(hexahydrobenzonitrile), 4,4'-azo-bis(4-cyanovaleric acid), 2,2'-azo-bis(2,4-dimethyl valeronitrile), and 2,2'-azo-bis(2-cyclopropyl propionitrile), 2,2'-azo-bis(2-cyclobutyl propionitrile), 2,2'-azo-bis(2-cyclobutyl propionitrile), 2,2'-azo-bis (2,4-dimethyl valeronitrile), 1,1'-azo-bis(1-cycloheptanenitrile), 2,2'-azo-bis(methylheptylonitrile), 2,2'-azo-bis(2-cyclohexyl propionitrile), azo-bis-isobutyramidine 2HCl, phenyl-azo-triphenylmethane, 4-hydroxyphenyl-azo-triphenylmethane, peroxide and peroxy compounds, such as benzoyl peroxide, tert-butyl peroxy pivalate, tert-amyl peroxypivalate, acetyl peroxide, propionyl peroxide, 2-isopropionyl peroxide, butyryl peroxide, diisobutyryl peroxide, dilauroyl peroxide, didecanoyl peroxide, cumyl peroxyneodecanoate, 1,1,3,3-tetramethylbutyl peroxyneodecanoate, tert-butyl peroxydiethylacetate, tert-amyl peroxy-2-ethylhexanoate, tert-amyl peroxy-2-ethylhexanoate, 2-methoxybenzoyl peroxide, cumyl peroxyneoheptanoate, tert-amyl peroxyneodecanoate, tert-butyl peroxyneodecanoate, tert-butyl peroxyneoheptanoate, tert-amyl peroxyacetate, 4-benzylidenebutyryl peroxide, methyl phthaloyl peroxide, 1,1-di(tert-amylperoxy)cyclohexane, 3,6,9-triethyl-3,6,9-trimethyl-1,4,7-triperoxonane, hydroperoxides such as Isopropylcumyl hydroperoxide, 1,1,3,3-tetramethylbutyl hydroperoxide, cumyl hydroperoxide, tert-Butyl hydroperoxide, tert-amyl hydroperoxide, carbonates such as diethyl peroxydicarbonate, tert-butylperoxy isopropyl carbonate, tert-butylperoxy 2-ethylhexyl carbonate, di-sec-butyl peroxydicarbonate, diisopropyl peroxydicarbonate, di(4-tert-butylcyclohexyl) peroxydicarbonate, di(2-ethylhexyl) peroxydicarbonate, dicetyl peroxydicarbonate, dimyristyl peroxydicarbonate, tert-amylperoxy 2-ethylhexyl carbonate, tert-butylperoxy isopropyl carbonate, tert-butylperoxy 2-ethylhexyl carbonate, ethyl tert-butyl peroxalate; benzyl (tert-butyl peroxy) oxalate; tertiary-butyl-N-(3-tolylperoxy) carbamate and per-salt compounds, such as potassium persulfate and mixtures thereof, wherein 2,2'-azo-bis(2-methyl propionitrile), 2,2'-azodi (2-methylbutyronitrile), dilauroyl peroxide, cumyl peroxyneodecanoate, tert-amyl peroxy-2-ethylhexanoate, tert-amyl peroxy-2-ethylhexanoate are especially preferred.

Process step B) in the process according to the instant invention is conducted in neat or in a solvent, preferably in solvent. The amount of solvent can vary from 1 to 95%, preferably from 5 to 50%, more preferably from 10 to 40%, wherein the weight percent refer to the total weight of the sum of all monomers (1) and (2) provided in process step A).

Possible solvents can be but not are limited to: alcohols like methanol, ethanol, isopropanol, butanol, hexanol, tert-butanol, isoamyl alcohol, glycol, hexylene glycol, propylenglycol, butylglycol, butyldiglycol, glycerine, ketones like ethylmethyl ketone, methylbutyl ketone, acetone, ester like methyl acetate, ethyl acetate, isopropylacetate, propyl acetate, butyl acetate, hexylacetate, isooctyl acetate, methoxypropylacetate, acids like formic acid, acetic acid, propionic acid, ether like diethylether, dibutylether, tert-butylmethylether, petroleum ether, tetrahydrofuran, dioxane, polyethers, carbonates like ethylencarbonate, propylencarbonate, dimethylcarbonate, diethylcarbonate, dipropylcarbonate, nitriles like benzonitrile, acetonitrile, toluene, xylene, ionic liquids, water, organic oils such as TEGOSOFT® types and mixtures thereof.

In process step B) in the process according to the instant invention at least one chain transfer agent can be present, preferably in an amount such that the weight ratio of added initiator in process step B) and chain transfer agent is in the range of 1:20 to 1:0.1, preferably 1:10 to 1:1.

The chain transfer agent preferably present in process step B) in the process according to the instant invention is selected from at least one of the group of tetrachloromethane, bromotrichloromethane, Isooctyl 3-mercaptopropionate, 4-methylbenzenethiol, tert-nonyl mercaptan, pentaerythritol tetrakis(2-mercaptoacetate), pentaerythritol tetrakis(3-mercaptopropionate), 4,4'-thiobisbenzenethiol, trimethylolpropane tris(3-mercaptopropionate), 1,8-dimercapto-3,6-dioxaoctane, n-dodecanethiol, ethyl mercaptan, mercaptoethanol, mercaptopropanol, mercaptobutanol, mercaptohexanol, mercaptooctanol, propanethiol, dithiothreitol, cysteine, homocysteine, glutathione, tert-dodecanethiol, thioglycolic acid, dimercaptosuccinic, 2,3-dimercapto-1-propanesulfonic acid, acetylcysteine and thiophenol.

In an alternative process according to the instant invention no chain transfer agent is present in the process.

Process step B) in the process according to the instant invention is preferably conducted at a temperature of 10° C. to 250° C., preferably of 20° C. to 200° C. and more preferably of 60° C. to 180° C.

Process step B) in the process according to the instant invention is preferably conducted at a pressure of 0.5 to 20 bar, more preferably from 1 to 5 bar and even more preferably at atmospheric pressure.

Process step B) in the process according to the instant invention is preferably conducted at a pH of 3 to 10, more preferably 4 to 9 and even more preferably 5 to 8. Process step B) in the process according to the instant invention is preferably can be conducted not only in daylight but also in the absence of light and is preferably conducted in the absence of light.

Process step C) in the process according to the instant invention serves the purpose to remove excess of monomers. Therefore, step C) in the process according to the instant invention is a chasing step with the addition of further initiator after completion of process step B), in order to remove excess of monomer. The additional initiator is preferably applied in concentrations of 0.01% to 5%, preferably 0.1 to 2.5%, more preferably 0.2% to 2%, wherein the weight percent refer to the total weight of the sum of all monomers (1) and (2) provided in process step A).

Process step D) in the process according to the instant invention can be a water steam distillation. Here, some water is applied to the solution in order to remove excess monomers from the reaction. The amount of added water can vary from 0.1 to 20%, preferably 0.5 to 10%, more preferably 1% to 5% wherein the weight percent refer to the total weight of the sum of all monomers (1) and (2) provided in process step A).

Further clean-up steps D) in the process according to the instant invention can be an extraction with water and/or organic solvents, a distillation with or without vacuum and/or recrystallization with water and/or organic solvents.

Both, a chasing step and a water steam distillation can both be applied in process step C).

A further subject matter of the present invention is a polymer obtainable by the process of the instant invention. The polymer obtainable by this process preferably is characterized in, that it has a number average molecular weight $M_n$ in the range of from 2,000 to 9,000 g/mol A further subject matter of the present invention is a personal care formulation containing at least one polymer of the instant invention or at least one polymer obtainable by the process of the instant invention.

Furthermore, the formulations according to the invention can comprise at least one additional component selected from the group of
emollients,
emulsifiers,
thickeners/viscosity regulators/stabilizers,
UV photoprotective filters,
antioxidants,
hydrotropes (or polyols),
solids and fillers,
film formers,
pearlescent additives, deodorant and antiperspirant active ingredients,
insect repellents,
self-tanning agents,
preservatives,
conditioners,
perfumes,
dyes,
odor absorbers,
cosmetic active ingredients,
care additives,
superfatting agents,
solid particles,
solvents,
wherein perfumes, solid particles, and/or UV photoprotective filters, especially organic filters, are preferably comprised.

The preferably comprised solid particles are characterized by having a mean particle size d50 of from 0.1 to 1000 μm.

The mean particle size d50 is preferably determined by light scattering in a laser beam with a Malvern Mastersizer 2000. The determination is done using the dry measurement. Each time 20 to 40 g powder are fed using a Scirocco dry powder feeder. The particle flow is controlled operating the vibrating tray with a feed-rate of 70%. The dispersive air pressure is adjusted to be 3 bar. Each measurement is accompanied by a measurement of the background (10 seconds/10,000 single measurements). The measurement time of the sample is 5 seconds (5,000 single measurements). The refraction index as well as the blue light value are fixed to be 1.52. The evaluation is done using the Mie-theory.

Substances which can be used as exemplary representatives of the individual groups to be comprised in the formulation according to the invention are known to the person skilled in the art and can be found for example in the German application DE 102008001788.4. This patent application is hereby incorporated by reference and thus forms part of the disclosure.

As regards further optional components and the amounts of these components used, reference is made expressly to the relevant handbooks known to the person skilled in the art, for example K. Schrader, "Grundlagen und Rezepturen der Kosmetika [Fundamentals and Formulations of Cosmetics]", 2nd edition, page 329 to 341, Hüthig Buch Verlag Heidelberg.

The amounts of the respective additives are dependent on the intended use.

Typical guide formulations for the respective applications are known prior art and are contained for example in the brochures of the manufacturers of the respective base materials and active ingredients. These existing formulations can generally be adopted unchanged. If required, however, the desired modifications can be undertaken without complication by means of simple experiments for the purposes of adaptation and optimization.

Instantly claimed is also the use of at least one polymer of the instant invention or at least one polymer obtainable by the process of the instant invention for forming a film on a surface, especially skin and/or hair.

Instantly claimed is also the use of at least one polymer of the instant invention or at least one polymer obtainable by the process of the instant invention for retaining a fragrance on a surface, especially skin and/or hair.

Instantly claimed is also the use of at least one polymer of the instant invention or at least one polymer obtainable by the process of the instant invention for giving a dry skin feel to formulations, especially emulsions.

Instantly claimed is also the use of at least one polymer of the instant invention or at least one polymer obtainable by the process of the instant invention for the dispersion of solid pigments.

The solid pigments are those preferably comprised in the formulation according to the present invention.

Two or more polymers according to the invention can be used together.

The examples adduced hereinafter describe the present invention by way of example, without any intention that the invention, the scope of application of which is apparent from the entirety of the description and the claims, be restricted to the embodiments specified in the examples.

EXAMPLES

Molecular Weight Determination by Gel Permeation Chromatography (GPC):

GPC can be utilized to enable identification of the molecular weight of polymer.

The sample was prepared by making a 10 mg/mL solution using tetrahydrofuran as the diluent. The sample prep was placed in the oven at 54° C. for ten minutes then on a wrist action shaker for 60 minutes to aid dissolution. Upon visual inspection, the sample appeared to be completely dissolved in the diluent. The sample prepared was analyzed using two 300×7.5 mm polypore columns (manufactured by Agilent Technologies), a Waters 2695 chromatographic system, tetrahydrofuran mobile phase and refractive index detection. The sample was filtered by 0.45 um Nylon filters prior to injecting into the liquid chromatograph.

The standards used for calibration are EasiVial narrow polystyrene (PS) standards from Agilent Technologies. Narrow polystyrene standards ranging from 2.520.000 to 162 Daltons were used for calibration. The system uses a PSS SECcurity 1260 RI detector. The PS calibration curve is used to determine the molecular weight averages. The recording of diagrams and determination of the different molecular weights is conducted by the Win GPC Unichrom 8.1 software.

Melting Point Determination by DSC:

This method describes a generalized procedure for determining the melting temperatures of polymers by Differential Scanning Calorimetry (DSC). The method is based on ASTM E7941 and ASTM D 34182. Calibration of the DSC is done in accordance with ASTM E 9672.

Chemicals:
Behenyl acrylate (abcr)
Stearyl acrylate (abcr)
Hexadecyl methacrylate (abcr)
2-hydroxyethyl acrylate (BASF)
4-hydroxybutyl acrylate (BASF)
Mercaptoethanol (abcr)
Isopropyl Alcohol (Aldrich)
2,2'-Azodi(2-methylbutyronitrile) (AMBN) (Akzo Nobel)
Dilauroyl peroxide (Akzo Nobel)
Deionized Water Example 1

175 g of Behenyl acrylate, 25 g of 2-hydroxyethyl acrylate and 0.4 g of AMBN were added within 60 minutes at 80° C. to 40 g of Isopropanol filled four-neck flask equipped with a KPG blade stirrer, an internal thermometer, two dropping funnel, reflux condenser and an extension for further two necks under agitation after oxygen was removed from the system through nitrogen purge for about 20 min. The mixture was stirred at 80° C. for further 3 hours. Afterwards the solvent was stripped off by vacuum distillation (<100 mbar) followed by addition of 1 g of Dilauroyl peroxide and reaction for 60 min at 110° C. This step was repeated. The batch is then cooled to 90° C. and a shot of deionized water is introduced and thoroughly mixed. The water is finally removed by vacuum distillation.

Mn=7300 g/mol, Mw=21000, Mw/Mn=2.8
Tm=65° C.

Example 2

155 g of Stearyl acrylate, 45 g of 2-hydroxyethyl acrylate and 0.4 g of AMBN were added within 90 minutes at 80° C. to 50 g of Isopropanol filled four-neck flask equipped with a KPG blade stirrer, an internal thermometer, two dropping funnel, reflux condenser and an extension for further two necks under agitation after oxygen was removed from the system through nitrogen purge for about 20 min. The mixture was stirred at 80° C. for further 3 hours. Afterwards the solvent was stripped off by vacuum distillation (<100 mbar) followed by addition 1 g of Dilauroyl peroxide and reaction for 60 min at 125° C. This step was repeated. The batch is then cooled to 90° C. and a shot of deionized water is introduced and thoroughly mixed. The water is finally removed by vacuum distillation.

Mn=7500 g/mol, Mw=19000, Mw/Mn=2.6
Tm=49° C.

Example 3

135 g of Behenyl acrylate, 65 g of 2-hydroxyethyl acrylate and 0.4 g of AMBN were added within 90 minutes at 80° C. to 50 g of Isopropanol filled four-neck flask equipped with a KPG blade stirrer, an internal thermometer, two dropping funnel, reflux condenser and an extension for further two necks under agitation after oxygen was removed from the system through nitrogen purge for about 20 min. The mixture was stirred at 80° C. for further 3 hours. Afterwards the solvent was stripped off by vacuum distillation (<100 mbar) followed by addition of Dilauroyl peroxide and reaction for 60 min at 125° C. This step was repeated. The batch is then cooled to 90° C. and a shot of deionized water is introduced. The water is removed by vacuum distillation.

Mn=7800 g/mol, Mw=23000, Mw/Mn=3.1
Tm=63° C.

Example 4

135 g of Behenyl acrylate, 65 g of 4-hydroxybutyl acrylate and 0.4 g of AMBN were added within 90 minutes at 80° C. to 50 g of Isopropanol filled four-neck flask equipped with a KPG blade stirrer, an internal thermometer, two dropping funnel, reflux condenser and an extension for further two necks under agitation after oxygen was removed from the system through nitrogen purge for about 20 min. The mixture was stirred at 80° C. for further 3 hours. Afterwards the solvent was stripped off by vacuum distillation (<100 mbar) followed by addition of Dilauroyl peroxide and reaction for 60 min at 125° C. This step was repeated. The batch is then cooled to 90° C. and a shot of deionized water is introduced. The water is removed by vacuum distillation.

Mn=8100 g/mol, Mw=25000, Mw/Mn=3.2
Tm=62° C.

Example 5

155 g of Hexadecyl methacrylate, 45 g of 2-hydroxyethyl methacrylate and 0.4 g of AMBN were added within 90 minutes at 80° C. to 50 g of Isopropanol filled four-neck flask equipped with a KPG blade stirrer, an internal thermometer, two dropping funnel, reflux condenser and an extension for further two necks under agitation after oxygen was removed from the system through nitrogen purge for about 20 min. The mixture was stirred at 80° C. for further 3 hours. Afterwards the solvent was stripped off by vacuum distillation (<100 mbar) followed by addition of Dilauroyl peroxide and reaction for 60 min at 125° C. This step was repeated. The batch is then cooled to 90° C. and a shot of deionized water is introduced. The water is removed by vacuum distillation.

Mn=7400 g/mol, Mw=18000, Mw/Mn=2.9
Tm=25° C.

Comparative Example

This example corresponds to US2016250137. To a resin kettle equipped with overhead stirrer and condenser was added 16 g of stearyl acrylate, 4 g of hydroxyethyl acrylate and 0.07 g of mercaptoethanol. The mixture in the resin kettle was heated to 110° C., and oxygen was removed from the system through nitrogen purge for about 30 min followed by addition of 0.35 g of t-amylperoxy 2-ethylhexanoate. After allowing sufficient time for any initial exotherm to abate, 64 g of stearyl acrylate, 16 g of hydroxyethyl acrylate, 0.28 g of mercaptoethanol and 1.38 g of were pumped into the reaction vessel over 60 to 90 minutes. The polymer mixture was allowed to continue reacting for further 60 minutes followed by addition of 0.7 g of t-butylperoxybenzoate and reaction for 60 min. The mixture was then put under reduced pressure for 60 minutes for removal of volatile residuals.

Mn=51000 g/mol Mw=220000 Mw/Mn=3.5
Tm=48° C.

All concentrations in the application examples are given in percent by weight. Customary homogenization processes known to the person skilled in the art were used to produce the emulsions. The emulsions were therefore produced typically by heating oil phase and water phase to 70-75° C. Subsequently, either the oil phase was stirred into the water, or oil phase and water phase were combined without stirring. The mixture was then homogenized using a suitable homogenizer (e.g. Ultraturrax) for about 1-2 minutes. Stabilizing polymers (e.g. carbomers) are preferably stirred into the emulsion as oil dispersion at temperatures of 50-60° C. The mixture is then briefly homogenized. Addition of further ingredients (e.g. preservatives, active ingredients) was preferably carried out at 40° C. If the formulations were preserved with organic acids, the pH of the emulsions was adjusted to about 5. If the formulations contained water-soluble organic sunscreens, the pH of the emulsions was adjusted to about 6.5-7.0.

Application Example 1: Sensory Evaluation of Cosmetic Formulations Containing Organic Polymer According to the Current Invention in Comparison to Organic Polymers not According to the Current Invention Hydroxyl-functionalized organic polymers according to the current invention have been found to have advantages with regard to skin feel. To illustrate the effect, oil-in-water (O/W) sun care emulsions according to the following table were prepared on 200 g scale. A vehicle formulation without organic polymer was prepared for reference. Another film forming organic polymer based on alternative chemistry (VP/Eicosene Copolymer) was also used as representative of organic polymer based on prior art.

| Phase | Raw material | 1 | 2 | 3 | 4 | 5 |
|---|---|---|---|---|---|---|
| A | TEGO ® Care PBS 6 (Polyglyceryl-6 Stearate, Polyglyceryl-6 Behenate) | 3.00 | 3.00 | 3.00 | 3.00 | 3.00 |
|  | TEGIN ® M Pellets (Glyceryl Stearate) | 0.50 | 0.50 | 0.50 | 0.50 | 0.50 |
|  | TEGO ® Alkanol 1618 (Cetearyl Alcohol) | 0.50 | 0.50 | 0.50 | 0.50 | 0.50 |
|  | TEGOSOFT ® XC (Phenoxyethyl Caprylate) | 3.00 | 3.00 | 3.00 | 3.00 | 3.00 |
|  | TEGOSOFT ® P (Isopropyl Palmitate) | 2.00 | 2.00 | 2.00 | 2.00 | 2.00 |
|  | Bis-Ethylhexyloxyphenol Methoxyphenyl Triazine (Tinosorb S, BASF) | 3.00 | 3.00 | 3.00 | 3.00 | 3.00 |
|  | Butyl Methoxydibenzoylmethane | 2.00 | 2.00 | 2.00 | 2.00 | 2.00 |
|  | Ethylhexyl Salicylate | 3.00 | 3.00 | 3.00 | 3.00 | 3.00 |
|  | Octocrylene | 4.00 | 4.00 | 4.00 | 4.00 | 4.00 |
|  | Homosalate | 3.00 | 3.00 | 3.00 | 3.00 | 3.00 |
|  | Organic polymer (example 1) |  | 3.00 |  |  |  |
|  | Organic polymer (example 2) |  |  | 3.00 |  |  |
|  | Organic polymer (comparative example) |  |  |  | 3.00 |  |
|  | VP/Eicosene Copolymer (Antaron V-220) |  |  |  |  | 3.00 |
| B | Glycerin | 3.00 | 3.00 | 3.00 | 3.00 | 3.00 |
|  | Aqua | ad 100 | ad 100 | ad 100 | ad 100 | ad 100 |
| C | TEGO ® Carbomer 341 ER (Acrylates/C10-30 Alkyl Acrylate Crosspolymer) | 0.20 | 0.20 | 0.20 | 0.20 | 0.20 |
|  | TEGOSOFT ® XC (Phenoxyethyl Caprylate) | 0.80 | 0.80 | 0.80 | 0.80 | 0.80 |
| D | Tromethamine (Trisaminomethane, 30% in water) | 0.60 | 0.60 | 0.60 | 0.60 | 0.60 |
| E | Aqua | 7.12 | 7.12 | 7.12 | 7.12 | 7.12 |
|  | Tromethamine | 0.88 | 0.88 | 0.88 | 0.88 | 0.88 |
|  | Phenylbenzimidazole Sulfonic Acid (Eusolex 232) | 2.00 | 2.00 | 2.00 | 2.00 | 2.00 |
| F | Phenoxyethanol, Ethylhexylglycerin (Euxyl PE 9010, Schülke & Mayr) | 0.70 | 0.70 | 0.70 | 0.70 | 0.70 |

Skin feel of the emulsions was evaluated by sensory panel testing. Thirteen trained panelists applied 20 μL of each formulation on a defined test area of approx. 10 cm$^2$ on the volar forearm, not knowing their composition. Formulations were distributed using a finger within the test area by circling movements until complete absorption (or maximum 60 circles). Evaluation of skin feel parameters took place during distribution and after five minutes of application. In particular, "dry feel" of formulations was evaluated by the skin feel parameters oiliness, waxiness and slipperiness. Dry feel is desirable in functional formulations like sun care emulsions which tend to give oily and slippery residue when containing organic UV filters. Therefore, in such systems low oiliness, high waxiness and low slipperiness is favored. People were asked to rank the five formulations with respect to these parameters, from 1 (most preferred) to 5 (least preferred). The overall ranking of the test formulations with respect to the skin feel parameters is summarized in the following table.

| Formulation | 1 | 2 | 3 | 4 | 5 |
|---|---|---|---|---|---|
| Dry feel preference | 5.0 | 1.2 | 1.8 | 2.3 | 3.7 |

In comparison, the vehicle formulation (formulation 1) was evaluated as the moist oily, least waxy and most slippery formulation (average rating 5.0). This oily and slippery skin feel was somewhat reduced when VP/Eicosene Copolymer was added (average rating 3.7). Also with organic polymer according to comparative example skin feel was further improved (average rating 2.3). However, when organic polymers according to example 1 and 2 were used, skin feel was particularly received as dry (average rating 1.2 and 1.8).

This experiment clearly shows that organic polymers according to the invention have most pronounced "dry feel" properties which makes them ideally suited for sun care applications, among others.

Application Example 2: Water Resistance Test of Cosmetic Formulations Containing Organic Polymer According to the Current Invention in Comparison to Organic Polymers not According to the Current Invention Hydroxyl-functionalized organic polymers according to the current invention have been found to present better film-forming properties compared to non-inventive organic polymers. To illustrate the effect, oil-in-water (O/W) sun care emulsions according to the following table were prepared on 200 g scale. A vehicle formulation without organic polymer was prepared for reference.

| Phase | Raw material | 1 | 2 | 3 | 4 |
|---|---|---|---|---|---|
| A | Mineral Oil (Drakeol 7 LT, Penreco) | 2.00 | 2.00 | 2.00 | 2.00 |
| | Cetearyl Alcohol, Polysorbate 60 (PolaWax NF, Croda) | 5.00 | 5.00 | 5.00 | 5.00 |
| | Steareth-2 (Brij S2-SO, Croda) | 0.50 | 0.50 | 0.50 | 0.50 |
| | Steareth-21 (Brij S721-SO, Croda) | 1.00 | 1.00 | 1.00 | 1.00 |
| | Cetyl Alcohol (Lanette 16, BASF) | 1.00 | 1.00 | 1.00 | 1.00 |
| | Ethylhexyl Methoxycinnamate (Uvinul MC 80, BASF) | 7.50 | 7.50 | 7.50 | 7.50 |
| | Benzophenone-3 (Eusolex 4360, Merck) | 6.00 | 6.00 | 6.00 | 6.00 |
| | Ethylhexyl Salicylate | 5.00 | 5.00 | 5.00 | 5.00 |
| | Organic polymer (example 1) | | 1.00 | | |
| | Organic polymer (example 2) | | | 1.00 | |
| | Organic polymer (comparative example) | | | | 1.00 |
| B | Aqua | ad 100 | ad 100 | ad 100 | ad 100 |
| | Xanthan Gum (Grindsted Xanthan 80, DuPont Danisco) | 0.30 | 0.30 | 0.30 | 0.30 |
| C | Propylene Glycol, Diazolidinyl Urea, Methylparaben, Propylparaben (Germaben II, Ashland) | 1.00 | 1.00 | 1.00 | 1.00 |

Two µL/cm$^2$ emulsion were applied to in vitro skin (VITRO-SKIN®, IMS Inc.) and let dry. A sun protection factor (SPF) water resistance test was conducted. First, SPF of in vitro skin was determined using Labsphere UV-1000 Ultraviolet Transmittance Analyzer. In vitro skin was then immersed in a water bath. The water was stirred using a hot plate and magnetic stir bar for 80 minutes at 300 rpm and 40° C. The skin was removed from the water bath, let dry and the SPF was determined again. The percentual loss of SPF (SPF after water immersion compared to SPF before water immersion) is summarized in the following table.

| Formulation | 1 | 2 | 3 | 4 |
|---|---|---|---|---|
| Loss of SPF (%) | 74 | 4 | 13 | 52 |

Interestingly, the emulsion with organic polymer according to comparative example (formulation 4) showed higher reduction of SPF value after water immersion, compared to emulsion with organic polymer according to example 1 and 2 (formulations 2 and 3).

Although the molecular weight of organic polymer according to comparative example is higher, the loss of SPF is also higher. This indicates weaker film forming properties which might be due to a weaker interaction of organic polymer according to comparative example with organic UV filters, than organic polymers according to the invention.

Application Example 3: Sun Protection Factor (SPF) Test of Cosmetic Formulations Containing Organic Polymer According to the Current Invention in Comparison to Organic Polymers not According to the Current Invention Hydroxyl-functionalized organic polymers according to the current invention have been found to present better compatibility with organic UV filters compared to non-inventive organic polymers. To illustrate the effect, oil-in-water (O/W) sun care emulsions according to the following table were prepared on 200 g scale. A vehicle formulation without organic polymer was prepared for reference. Another film forming organic polymer based on alternative chemistry (VP/Eicosene Copolymer) was used as common benchmark and representative of organic polymer based on prior art.

| Phase | Raw material | 1 | 2 | 3 | 4 | 5 |
|---|---|---|---|---|---|---|
| A | TEGO ® Care PBS 6 (Polyglyceryl-6 Stearate, Polyglyceryl-6 Behenate) | 3.00 | 3.00 | 3.00 | 3.00 | 3.00 |
| | TEGIN ® M Pellets (Glyceryl Stearate) | 0.50 | 0.50 | 0.50 | 0.50 | 0.50 |
| | TEGO ® Alkanol 1618 (Cetearyl Alcohol) | 0.50 | 0.50 | 0.50 | 0.50 | 0.50 |
| | TEGOSOFT ® XC (Phenoxyethyl Caprylate) | 3.00 | 3.00 | 3.00 | 3.00 | 3.00 |
| | TEGOSOFT ® P (Isopropyl Palmitate) | 2.00 | 2.00 | 2.00 | 2.00 | 2.00 |
| | Bis-ethylhexyloxyphenol Methoxyphenyl Triazine (Tinosorb S, BASF) | 3.00 | 3.00 | 3.00 | 3.00 | 3.00 |
| | Butyl Methoxydibenzoylmethane | 2.00 | 2.00 | 2.00 | 2.00 | 2.00 |
| | Ethylhexyl Salicylate | 3.00 | 3.00 | 3.00 | 3.00 | 3.00 |
| | Octocrylene | 4.00 | 4.00 | 4.00 | 4.00 | 4.00 |
| | Homosalate | 3.00 | 3.00 | 3.00 | 3.00 | 3.00 |
| | Organic polymer (example 1) | | 3.00 | | | |
| | Organic polymer (example 2) | | | 3.00 | | |
| | Organic polymer (comparative example) | | | | 3.00 | |
| | VP/Eicosene Copolymer (Antaron V-220) | | | | | 3.00 |
| B | Glycerin | 3.00 | 3.00 | 3.00 | 3.00 | 3.00 |
| | Aqua | ad 100 | ad 100 | ad 100 | ad 100 | ad 100 |
| C | TEGO ® Carbomer 341 ER (Acrylates/C10-30 Alkyl Acrylate Crosspolymer) | 0.20 | 0.20 | 0.20 | 0.20 | 0.20 |
| | TEGOSOFT ® XC (Phenoxyethyl Caprylate) | 0.80 | 0.80 | 0.80 | 0.80 | 0.80 |

-continued

| Phase | Raw material | 1 | 2 | 3 | 4 | 5 |
|---|---|---|---|---|---|---|
| D | Tromethamine (Trisaminomethane, 30% in water) | 0.60 | 0.60 | 0.60 | 0.60 | 0.60 |
| E | Phenylbenzimidazole Sulfonic Acid | 2.00 | 2.00 | 2.00 | 2.00 | 2.00 |
|   | Tromethamine | 0.88 | 0.88 | 0.88 | 0.88 | 0.88 |
|   | Aqua | 7.12 | 7.12 | 7.12 | 7.12 | 7.12 |
| F | Phenoxyethanol, Ethylhexylglycerin (Euxyl PE 9010, Schülke & Mayr GmbH) | 0.70 | 0.70 | 0.70 | 0.70 | 0.70 |

One mg/cm$^2$ emulsion was applied to Polymethylmethacrylate (PMMA) plates (7.0×3.5 cm, 2 µm roughness, Schönberg GmbH &Co. KG) and let dry. A sun protection factor (SPF) test was conducted using a Labsphere UV-2000S Ultraviolet Transmittance Analyzer.

SPF efficiency (SPF/% of sunscreen used) of the individual formulations is summarized in the following table.

| Formulation | 1 | 2 | 3 | 4 | 5 |
|---|---|---|---|---|---|
| SPF efficiency | 2.0 | 2.6 | 2.5 | 2.3 | 2.3 |

The vehicle formulation (formulation 1) yielded a SPF efficiency of 2.0 which was increased in case organic polymer was used, which can be mainly contributed to the interaction of organic polymer with organic UV filter. The commonly employed benchmark VP/Eicosene Copolymer (formulation 5) increased SPF efficiency to 2.3, which was identical to the effect of organic polymer according to comparative example (formulation 4). Interestingly, emulsions with organic polymer according to example 1 and 2 (formulations 2 and 3) increased SPF efficiency further to 2.6 and 2.5, respectively. This effect indicates an even stronger interaction or organic polymer according to the current invention with organic UV filters, compared to non-inventive organic polymers.

Application Example 4: Processing of Cosmetic Formulations Containing Organic Polymer According to the Current Invention in Comparison to Organic Polymers not According to the Current Invention Hydroxyl-functionalized organic polymers according to the current invention have been found to have advantages with regard to processing in cosmetic emulsions compared to non-inventive organic polymers. To illustrate the effect, water-in-oil (W/O) emulsions according to the following table were prepared on 200 g scale. Phase A was heated to 80-90° C. and phase B (hot/cold processing [h/c]: room temperature, hot/hot processing [h/h]: 80° C.) was added during 120 seconds to phase A under stirring using a double-stage pulse counter-current stirrer at 500 rpm. The mixture is pre-homogenized during one minute at 1500 rpm, before cooling in a water bath to 40° C. followed by addition of phase C. Final homogenization is conducted below 30° C. during 120 seconds at 1500 rpm.

A vehicle formulation without organic polymer and using increased amount of cosmetic waxes instead was prepared for reference as a "standard procedure".

| | | W/O emulsion | | | |
|---|---|---|---|---|---|
| Phase | Raw material | 1 | 2 | 3 | 4 |
| A | ABIL ® EM 90 (Cetyl PEG/PPG-10/1 Dimethicone Triglyceride) | 2.50 | 2.50 | 2.50 | 2.50 |
|   | TEGOSOFT ® OP (Ethylhexyl Palmitate) | 5.00 | 5.00 | 5.00 | 5.00 |
|   | TEGOSOFT ® CT (Caprylic/Capric Triglyceride) | 10.00 | 10.00 | 10.00 | 10.00 |
|   | TEGOSOFT ® DEC (Diethylhexyl Carbonate) | 10.00 | 10.00 | 10.00 | 10.00 |
|   | Microcrystalline Wax (Paracera W 80, Paramelt) | 1.60 | 0.10 | 0.10 | 0.10 |
|   | Hydrogenated Castor Oil | 1.60 | 0.10 | 0.10 | 0.10 |
|   | Organic polymer (example 1) | | 3.00 | | |
|   | Organic polymer (example 2) | | | 3.00 | |
|   | Organic polymer (comparative example) | | | | 3.00 |
| B | Aqua | ad 100 | ad 100 | ad 100 | ad 100 |
|   | Sodium Chloride | 0.50 | 0.50 | 0.50 | 0.50 |
| C | Phenoxyethanol, Ethylhexylglycerin (Euxyl PE 9010, Schülke & Mayr GmbH) | 0.70 | 0.70 | 0.70 | 0.70 |

Observations during processing of W/O emulsions containing organic polymer according to the current invention (formulation 2, 3) and non-inventive organic polymer (formulation 4), all compared to "standard procedure" (formulation 1), are noted in the table below:

| Phase | Raw material | 1 | 2 | 3 | 4 |
|---|---|---|---|---|---|
| A | ISOLAN ® GPS (Polyglyceryl-4 Diisostearate/Polyhydroxystearate/Sebacate) | 4.0 | 4.0 | 4.0 | 4.0 |
|   | TEGOSOFT ® AC (Isoamyl Cocoate) | 6.0 | 6.0 | 6.0 | 6.0 |
|   | TEGOSOFT ® DC (Decyl Cocoate) | 8.0 | 8.0 | 8.0 | 8.0 |
|   | TEGOSOFT ® CT (Caprylic/Capric Triglyceride) | 4.0 | 4.0 | 4.0 | 4.0 |
|   | CI 77891, Triethoxycaprylylsilane (Unipure White LC 981 AS-EM, Sensient) | 5.0 | 5.0 | 5.0 | 5.0 |
|   | CI 77492, Triethoxycaprylylsilane (Unipure Yellow LC 182 AS-EM, Sensient) | 0.6 | 0.6 | 0.6 | 0.6 |
|   | CI 77491 & Triethoxycaprylylsilane (Unipure Red LC 381 AS-EM, Sensient) | 0.35 | 0.35 | 0.35 | 0.35 |
|   | CI 77499 & Triethoxycaprylylsilane (Unipure Black LC 989 AS-EM, Sensient) | 0.1 | 0.1 | 0.1 | 0.1 |
| B | Beeswax | 0.5 | 0.5 | 0.5 | 0.5 |
|   | Hydrogenated Castor Oil | 0.5 | 0.5 | 0.5 | 0.5 |
|   | Organic polymer (example 1) |  | 3.00 |  |  |
|   | Organic polymer (example 2) |  |  | 3.00 |  |
|   | Organic polymer (comparative example) |  |  |  | 3.00 |
|   | dermosoft GMC (Glyceryl Caprate) | 0.5 | 0.5 | 0.5 | 0.5 |
| C | Aqua | ad 100 | ad 100 | ad 100 | ad 100 |
|   | Zinc Sulfate Heptahydrate | 2.0 | 2.0 | 2.0 | 2.0 |
|   | Glycerin | 3.0 | 3.0 | 3.0 | 3.0 |
|   | Citric Acid (10% in water) | q.s. | q.s. | q.s. | q.s. |

| Formulation | 2 | 3 | 4 |
|---|---|---|---|
| Remarks | h/c: okay<br>h/h: okay | h/c: okay<br>h/h: okay | h/c: slower uptake of phase B<br>h/h: crystallization during cooling to 40° C., phase separation upon final homogenization |

Interestingly, the final emulsion with organic polymer according to comparative example (formulation 4) was not formed under hot/hot processing conditions, although the melting point/crystallization temperature of organic polymer according to comparative example and example 2 are similar (48° C., 49° C.) and only the melting point of organic polymer according to example 1 is higher (65° C.). Also under hot/cold processing conditions, addition of water phase to oil phase was delayed during processing of formulation containing organic polymer according to comparative example.

This application example clearly shows that the properties of organic polymers according to the current invention have advantages with respect to processing in cosmetic W/O emulsions, compared to non-inventive organic polymers.

Application Example 5: Pigment Dispersion in Cosmetic Formulations Containing Organic Polymer According to the Current Invention in Comparison to Organic Polymers not According to the Current Invention Hydroxyl-functionalized organic polymers according to the current invention have been found to have advantages with regard to pigment dispersion. To illustrate the effect, water-in-oil (W/O) color cosmetic emulsions according to the following table were prepared on 200 g scale. A vehicle formulation without organic polymer was prepared for reference.

Color of emulsions was measured using a Dr. Lange Micro Color LMG140 colorimeter and Lab color space. The combination of white, yellow, red and black pigments yields a skin-colored emulsion, which is typical for foundations. A better pigment dispersion gives a more intense color, indicated by increased 'a' (red) color component, which are summarized in the following table.

| Formulation | 1 | 2 | 3 | 4 |
|---|---|---|---|---|
| a color component | 11.2 | 14.5 | 14.0 | 12.8 |

When organic polymer according to comparative example was used (formulation 4), red color component was increased compared to vehicle formulation ($\Delta a=1.6$), indicating slightly improved pigment distribution in the oil phase. However, when organic polymer according to example 1 and 2 was used (formulations 2 and 3), color difference was higher ($\Delta E=3.3$ and 2.8), indicating even improved distribution of the organo-modified pigments in the oil phase. This experiment shows that organic polymers according to the current invention are better to achieve more even pigment distribution, which makes them ideally suited for color cosmetics applications, among others.

Application Example 6: Fragrance Oil Retention Test of Cosmetic Formulations Containing Organic Polymer According to the Current Invention in Comparison to Organic Polymers not According to the Current Invention Hydroxyl-functionalized organic polymers according to the current invention have been found to present better fragrance retention properties compared to non-inventive organic polymers. To illustrate the effect, conditioner formulations according to the following table were prepared on 200 g scale. A vehicle formulation without organic polymer was prepared for reference.

| Phase | Raw material | 1 | 2 | 3 | 4 |
|---|---|---|---|---|---|
| A | TEGINACID ® C (Ceteareth-25) | 0.50 | 0.50 | 0.50 | 0.50 |
| | TEGO ® Alkanol 1618 (Cetearyl Alcohol) | 5.00 | 5.00 | 5.00 | 5.00 |
| | Organic polymer (example 3) | | 3.00 | | |
| | Organic polymer (example 2) | | | 3.00 | |
| | Organic polymer (comparative example) | | | | 3.00 |
| B | Aqua | ad 100 | ad 100 | ad 100 | ad 100 |
| | Citric Acid (10% in water) | q.s. | q.s. | q.s. | q.s. |
| C | Perfume (Powder Fruit, Frey & Lau) | 0.50 | 0.50 | 0.50 | 0.50 |
| | Methylisothiazolinone, Phenoxyethanol (Neolone PE) | 0.45 | 0.45 | 0.45 | 0.45 |

The fragrance retention test was conducted using standardized human hair tresses (4 g, caucasian hair, Kerling Int., Germany). Hair tresses were pre-treated by bleaching. Bleaching powder (e.g. "blondor special", Wella) and hydrogen peroxide (e.g. "Welloxyd 9%", Wella) were mixed to a paste (weight ratio powder:hydrogen peroxide=2:3). The paste was applied to hair tresses with a brush. After exposure time of 30 min at room temperature hair tresses were washed under running water of approx. 37° C. for two minutes. Subsequently, hair tresses were washed with a shampoo (12% Sodium Laureth Sulfate in water, 3% Sodium Chloride; 0.25 g shampoo/g hair) for one minute and then rinsed for one minute. The procedure was repeated one time. After the second washing step hair tresses were rinsed for two minutes. Pre-damaged hair was equilibrated overnight at 50% relative humidity and 22° C. Before application of test formulation the hair tress was soaked by flowing water of approx. 37° C. Water was squeezed out between the fingers, then the conditioner formulation was applied (0.1 g/g hair) and rubbed softly onto the hair. After a leave-in time of one minute the hair tress was rinsed under flowing water for one minute. Treated hair was equilibrated for 12 h at 50% relative humidity and 22° C.

Paired hair tresses were provided blinded and in random order to a collective of twelve trained panelists so that each combination of pairs (hair tresses treated with formulation 1 and 2, 1 and 3, 1 and 4, 2 and 3, 2 and 4, 3 and 4) was evaluated twice. Panelists were asked to differentiate between hair tress with higher fragrance intensity (ranking 1) from lower intensity (ranking 2). A ranking of 1.5 was assigned to both hair tresses in case no difference was observed. The average rankings are summarized in the following table.

| Formulation | 1 | 2 | 3 | 4 |
|---|---|---|---|---|
| | 1.92 | 1.17 | 1.25 | 1.67 |

When hair tress was evaluated with vehicle (formulation 1) an average ranking of 1.92 was obtained, which corresponds to least preference. When organic polymer according to comparative example was used (formulation 4), preference was slightly higher (ranking 1.67), indicating improved fragrance retention. However, when organic polymer according to example 1 and 2 was used (formulations 2 and 3), preference was highest (ranking 1.17 and 1.25), indicating even improved retention of fragrance oil on hair. This effect could be due to an improved solubilization of fragrance in the formulation and therefore better coverage of the hair, or due to an improved interaction of hair, fragrance oil and organic polymer resulting in better retention of fragrance on hair.

Example Formulations

| AP/Deo stick | | |
|---|---|---|
| Phase | Raw material | w/w-% |
| A | PPG-14 Butyl Ether | 28.50 |
| | Cylcohexasiloxane; Cyclopentasiloxane | 5.10 |
| | C12-15 Alkyl Benzoate | 5.30 |
| | Hydrogenated Castor Oil | 4.80 |
| | Organic Polymer (Example 1) | 5.00 |
| | Stearyl Alcohol | 28.00 |
| | Aluminium Zirconium Tetrachlorohydrex Gly | 23.10 |
| | Isopropylparaben, Isobutylparaben, Butylparaben | 0.20 |

| AP/Deo roll-on | | |
|---|---|---|
| Phase | Raw material | w/w-% |
| A | Organic Polymer (Example 3) | 5.00 |
| | Mineral Oil | 4.00 |
| | Cyclopentasiloxane | 11.50 |
| | PEG-30 Dipolyhydroxystearate | 1.00 |
| B | Magnesium Sulfate | 0.50 |
| | Glycerin | 5.00 |
| | Aqua | ad 100 |
| | Aluminium Chlorohydrate (20% in water) | 40.00 |

| Deo Roll-on, PEG-free, ACH-free | | |
|---|---|---|
| Phase | Raw material | w/w-% |
| A | TEGO ® Care PS (Methyl Glucose Sesquistearate) | 1.75 |
| | TEGO ® Care PL 4 (Polyglyceryl-4 Laurate) | 0.25 |
| | TEGOSOFT ® AC (Isoamyl Cocoate) | 1.00 |
| | TEGOSOFT ® CT (Caprylic/Capric Triglyceride) | 1.00 |
| | Organic Polymer (Example 3) | 1.00 |
| | TEGO ® Feel C 10 (Cellulose) | 1.00 |
| | Triethyl Citrate | 5.00 |
| | Caproyl/Lauroyl Lactyl Lactate (Dermosoft decalact liquid, Dr. Straetmans) | 1.00 |
| B | Aqua | ad 100 |
| | Glycerin | 3.00 |
| | Hydroxyethyl Cellulose (Natrosol 250 HHR, Aqualon) | 1.00 |
| C | Aqua | 0.57 |
| | Sodium Hydroxide | 0.03 |
| | p-Anisic Acid (Dermosoft 688, Dr. Straetmans) | 0.10 |
| | Glycerin | 0.30 |
| D | Citric Acid (10% in water) | q.s. |

Sun Care SPF 30 spray

| Phase | Raw material | w/w-% |
|---|---|---|
| A | TEGO ® Care PBS 6 (Polyglyceryl-6 Stearate, Polyglyceryl-6 Behenate) | 3.00 |
| | TEGOSOFT ® TN (C12-15 Alkyl Benzoate) | 3.00 |
| | Organic Polymer (Example 2) | 0.50 |
| | Bis-ethylhexyloxyphenol Methoxyphenyl Triazine (Tinosorb S, BASF) | 3.00 |
| | Butyl Methoxydibenzoylmethane | 2.00 |
| | Homosalate | 4.00 |
| | Ethylhexyl Salicylate | 4.00 |
| | Octocrylene | 4.00 |
| | TEGO ® Feel C 10 (Cellulose) | 1.00 |
| B | Aqua | ad 100 |
| | Gellan Gum (Kelcogel CG-HA, CP Kelco) | 0.03 |
| | EDTA | 0.05 |
| | Glycerin | 3.00 |
| C | Phenylbenzimidazole Sulfonic Acid | 2.00 |
| | Tromethamine | 0.88 |
| | Aqua | 7.12 |
| D | TEGO ® Carbomer 341 ER (Acrylates/C10-30 Alkyl Acrylate Crosspolymer) | 0.20 |
| | Aqua | 9.80 |
| E | Tromethamine (Trisaminomethane, 30% in water) | q.s. |
| F | Phenoxyethanol, Ethylhexylglycerin (Euxyl PE 9010, Schülke & Mayr GmbH) | 0.70 |

Oil Release Sun Care Lotion SPF 50

| Phase | Raw material | w/w-% |
|---|---|---|
| A | TEGO ® Care PBS 6 (Polyglyceryl-6 Stearate, Polyglyceryl-6 Behenate) | 3.00 |
| | TEGOSOFT ® TN (C12-15 Alkyl Benzoate) | 15.00 |
| | TEGOSOFT ® DEC (Diethylhexyl Carbonate) | 10.00 |
| | TEGOSOFT ® XC (Phenoxyethyl Caprylate) | 10.00 |
| | Organic Polymer (Example 2) | 1.00 |
| | Diethylamino Hydroxybenzoyl Hexyl Benzoate (Uvinul A plus, BASF) | 10.00 |
| | Ethylhexyl Methoxycinnamate | 10.00 |
| | Bis-Ethylhexyloxyphenol Methoxyphenyl Triazine (Tinosorb S, BASF) | 5.00 |
| | Ethylhexyl Salicylate | 5.00 |
| | Homosalate | 5.00 |
| | TEGO ® Feel C 10 (Cellulose) | 1.00 |
| B | Aqua | ad 100 |
| | Glycerin | 3.00 |
| C | Phenoxyethanol, Ethylhexylglycerin (Euxyl PE 9010, Schülke & Mayr GmbH) | 0.70 |
| D | Citric Acid (10% in water) | q.s. |

Sun Care Spray SPF 30

| Phase | Raw material | w/w-% |
|---|---|---|
| A | TEGOSOFT ® XC (Phenoxyethyl Caprylate) | 20.00 |
| | TEGOSOFT ® TN (C12-15 Alkyl Benzoate) | 8.00 |
| | TEGOSOFT ® APM (PPG-3 Myristyl Ether) | 8.00 |
| | Organic Polymer (Example 1) | 0.50 |
| | TEGO ® Xymenynic (Caprylic/Capric Triglyceride; Xymenynic Acid) | 2.00 |
| | Octocrylene | 6.80 |
| | Ethylhexyl Salicylate | 2.50 |
| | Butyl Methoxydibenzoylmethane | 5.00 |
| | Bis-Ethylhexyloxyphenol Methoxyphenyl Triazine (Tinosorb S, BASF SE) | 3.00 |
| | Diethylhexyl Butamido Triazone | 1.20 |
| B | Alcohol | ad 100 |

Cooling After Sun Gel

| Phase | Raw material | w/w-% |
|---|---|---|
| A | TEGOSOFT ® SH (Stearyl Heptanoate) | 5.00 |
| | TEGOSOFT ® AC (Isoamyl Cocoate) | 5.00 |
| | Organic Polymer (Example 1) | 0.20 |
| | TEGO ® Carbomer 341 ER (Acrylates/C10-30 Alkyl Acrylate Crosspolymer) | 0.20 |
| | TEGO ® Carbomer 140 (Carbomer) | 0.20 |
| | TEGOLON ® 12-20 (Nylon-12) | 0.30 |
| B | Aqua | ad 100 |
| | Glycerin | 2.00 |
| | HyaCare ® (Sodium Hyaluronate) | 3.00 |
| | TEGO ® Cosmo C 100 (Creatine) | 0.50 |
| C | Ethanol | 2.00 |
| D | Sodium Hydroxide (10% in water) | 1.80 |
| E | Dipropylene Glycol; Methylparaben; Ethylparaben; Aqua; Methylisothiazolinone (Microcare MEM, Thor) | 0.80 |
| Z | Perfume | q.s. |

Light O/W Sun Care Lotion

| Phase | Raw material | w/w-% |
|---|---|---|
| A | AXOL ® C 62 Pellets (Glyceryl Stearate Citrate) | 2.50 |
| | TEGO ® Alkanol 1618 (Cetearyl Alcohol) | 1.00 |
| | TEGOSOFT ® XC (Phenoxyethyl Caprylate) | 8.00 |
| | Isoadipate (Diisopropyl Adipate) | 1.00 |
| | Butyloctyl Salicylate (HallBrite BHB, The HallStar Company) | 2.00 |
| | Tocopheryl Acetate | 0.20 |
| | Dimethicone (5 mPas) | 1.00 |
| | Butyl Methoxydibenzoylmethane | 1.50 |
| | Diethylamino Hydroxybenzoyl Hexyl Benzoate (Uvinul A Plus, BASF) | 4.00 |
| | Ethylhexyl Triazone | 2.00 |
| | Ethylhexyl Salicylate | 5.00 |
| | Octocrylene | 8.00 |
| | Organic Polymer (Example 3) | 0.50 |
| B | TEGO ® Sun T 805 (Titanium Dioxide; Trimethoxycaprylylsilane) | 1.00 |
| C | Glycerin | 3.20 |
| | EDTA | 0.02 |
| | Aqua | ad 100 |
| D | TEGO ® Carbomer 341 ER (Acrylates/C10-30 Alkyl Acrylate Crosspolymer) | 0.10 |
| | TEGOSOFT ® XC (Phenoxyethyl Caprylate) | 0.90 |
| E | Sodium Hydroxide (10% in water) | q.s |
| Z | Preservative, Perfume | q.s |

W/O Foundation

| Phase | Raw material | w/w-% |
|---|---|---|
| A | Bis-(Glyceryl/Lauryl) Glyceryl Lauryl Dimethicone (and) Caprylic/Capric Triglyceride | 4.00 |
| | Isododecane | 3.33 |
| | TEGOSOFT ® XC (Phenoxyethyl Caprylate) | 3.33 |
| | Cyclomethicone | 3.33 |
| | Organic Polymer (Example 1) | 2.00 |
| | CI 77891, Titanium Dioxide, Alumina, Triethoxycaprylylsilane (HOMBITAN AC360, Sachtleben) | 4.00 |
| | CI 77491, CI 77492, CI 77499 (Iron Oxide, Sicovit Brown 70 E 172, Rockwood Pigments) | 2.50 |
| | Talc | 2.00 |
| B | Dicaprylyl Carbonate, Stearalkonium Hectorite, Propylene Carbonate (Cosmedia Gel CC, BASF SE) | 3.00 |
| | Isododecane | 1.50 |
| | TEGOSOFT ® XC | 1.50 |
| | Cyclomethicone | 1.50 |

W/O Foundation

| Phase | Raw material | w/w-% |
|---|---|---|
| C | Glycerin | 5.00 |
|   | Magnesium Sulfate Heptahydrate | 1.50 |
|   | Aqua | ad 100 |
| D | Phenoxyethanol, Methylparaben, Propylparaben, Ethylparaben (Phenonip XB, Clariant) | 0.70 |
|   | Boron Nitride (Boroneige 1201, ESK) | 5.00 |

Dry Touch Hand Moisturizing Cream

| Phase | Raw material | w/w-% |
|---|---|---|
| A | VARISOFT ® TA 100 (Distearyldimonium Chloride) | 3.00 |
|   | Stearyl Alcohol | 1.00 |
|   | TEGIN ® M Pellets (Glyceryl Stearate) | 1.00 |
|   | TEGOSOFT ® SH (Stearyl Heptanoate) | 1.00 |
|   | TEGOSOFT ® TN (C12-15 Alkyl Benzoate) | 5.00 |
|   | Organic Polymer (Example 2) | 2.00 |
|   | Diethylamino Hydroxybenzoyl Hexyl Benzoate (Uvinul A plus, BASF) | 3.00 |
|   | Ethylhexyl Salicylate | 3.00 |
|   | Ethylhexyl Methoxycinnamate | 5.00 |
|   | Tocopheryl Acetate | 0.50 |
|   | TEGO ® Feel C 10 | 1.00 |
| B | Aqua | ad 100 |
|   | Glycerin | 3.00 |
| C | TEGO ® Natural Betaine (Betaine) | 2.00 |
|   | Aqua | 2.00 |
| D | Phenoxyethanol, Ethylhexylglycerin (Euxyl PE 9010, Schülke & Mayr GmbH) | 0.70 |

Color cosmetics formulation

| Phase | Raw material | w/w-% |
|---|---|---|
| A | Cetyl PEG/PPG-10/1 Dimethicone; Polyglyceryl-4 Isostearate | 3.00 |
|   | ABIL ® 350 (Dimethicone) | 1.50 |
|   | Isohexadecane | 6.70 |
|   | TEGOSOFT ® DEC (Diethylhexyl Carbonate) | 5.00 |
|   | Organic Polymer (Example 3) | 2.00 |
|   | CI 77891, Titanium Dioxide, Alumina, Triethoxycaprylylsilane (HOMBITAN AC360, Sachtleben) | 8.00 |
|   | CI 77499, Iron Oxides, Dimethicone (SA-C335000-10, Miyoshi Kasei) | 1.80 |
|   | Talc | 2.00 |
| B | Disteardimonium Hectorite (Bentone 38V CG, Elementis Specialties) | 1.50 |
|   | Aluminum Starch Octenylsuccinate (Dry-Flo PC, AkzoNobel) | 1.50 |
|   | TEGOLON ® 12-10 (Nylon-12) | 1.50 |
|   | TEGOSOFT ® DEC (Diethylhexyl Carbonate) | 2.00 |
| C | Glycerin | 2.00 |
|   | Sodium Chloride | 0.80 |
|   | Aqua | ad 100 |
| D | Phenoxyethanol, Methylparaben, Propylparaben, Ethylparaben (Phenonip XB, Clariant) | 0.80 |

Age Defense BB Cream SPF 15

| Phase | Raw material | w/w-% |
|---|---|---|
| A | TEGIN ® 4100 Pellets (Glyceryl Stearate) | 1.00 |
|   | Stearic Acid | 0.50 |
|   | TEGO ® Alkanol 18 (Stearyl Alcohol) | 1.00 |
|   | TEGOSOFT ® DEC (Diethylhexyl Carbonate) | 6.90 |
|   | Organic Polymer (Example 2) | 3.00 |
|   | HyaCare ® Filler CL (Aqua; Ethylhexyl Stearate; Sodium Hyaluronate Crosspolymer; Polyglyceryl-4 Diisostearate/Polyhydroxystearate/Sebacate; Sodium Isostearate) | 2.00 |
|   | Phytosphingosine | 0.10 |
|   | Ethylhexyl Methoxycinnamate | 5.00 |
|   | Diethylamino Hydroxybenzoyl Hexyl Benzoate | 3.00 |
| B | Titanium Dioxide (Hombitan AC 360, Sachtleben) | 3.00 |
|   | Talc (Micro Talc IT Extra-AW, Mondo Minerals B.V.) | 2.00 |
|   | Unipure Yellow LC 182 | 0.36 |
|   | Unipure Red LC 381 | 0.12 |
|   | Unipure Black LC 989 | 0.08 |
|   | TEGOSOFT ® AC (Isoamyl Cocoate) | 4.44 |
|   | TEGOSOFT ® XC (Phenoxyethyl Caprylate) | 4.00 |
|   | Polymethyl Methacrylate (Sepimat P, Seppic) | 3.00 |
| C | Aqua | ad 100 |
|   | Glycerin | 3.00 |
|   | TEGO ® Care CG 90 (Cetearyl Glucoside) | 1.00 |
|   | HyaCare ® 50 (Hydrolyzed Hyaluronic Acid) | 0.10 |
|   | TEGO ® Pep 4-17 (Tetrapeptide-21; Glycerin; Butylene Glycol; Aqua) | 2.00 |
| D | Alcohol | 3.00 |
| E | Microcare MEM (Dipropylene Glycol; Methylparaben; Ethylparaben; Aqua; Methylisothiazolinone) | 0.80 |

Moisture Caring BB Cream SPF 15

| Phase | Raw material | w/w-% |
|---|---|---|
| A | ABIL ® EM 180 (Cetyl PEG/PPG-10/1 Dimethicone) | 2.00 |
|   | ABIL ® Wax 9801 (Cetyl Dimethicone) | 2.00 |
|   | Diethylamino Hydroxybenzoyl Hexyl Benzoate; Ethylhexyl Methoxycinnamate | 10.00 |
|   | Cyclomethicone | 2.00 |
|   | Organic Polymer (Example 1) | 3.00 |
|   | HyaCare ® Filler CL (Aqua; Ethylhexyl Stearate; Sodium Hyaluronate Crosspolymer; Polyglyceryl-4 Diisostearate/Polyhydroxystearate/Sebacate; Sodium Isostearate) | 2.00 |
|   | Phytosphingosine (Phytosphingosine) | 0.10 |
|   | Hydrogenated Castor Oil | 0.50 |
|   | Microcrystalline Wax | 0.50 |
| B | Talc (Micro Talc IT Extra-AW, Mondo Minerals B.V.) | 2.00 |
|   | Titanium Dioxide (Hombitan AC 360, Sachtleben) | 4.00 |
|   | Unipure Yellow LC 182 | 0.36 |
|   | Unipure Red LC 381 | 0.12 |
|   | Unipure Black LC 989 | 0.08 |
|   | AEROSIL R 972 (Silica Dimethylsilylate) | 0.50 |
|   | TEGOLON ® ECO 10-10 (Nylon-10/10) | 2.00 |
|   | TEGOSOFT ® OS (Ethylhexyl Stearate) | 5.00 |
|   | TEGOSOFT ® DEC (Diethylhexyl Carbonate) | 6.00 |
| C | Aqua | ad 100 |
|   | HyaCare ® (Sodium Hyaluronate) | 0.05 |
|   | Glycerin | 5.00 |
|   | Sodium Chloride | 0.80 |
| D | Phenoxyethanol; Ethylhexylglycerin (EUXYL PE 9010, Schülke & Mayr) | 0.70 |

W/O emulsion

| Phase | Raw material | w/w-% |
|---|---|---|
| A | ISOLAN ® GPS (Polyglyceryl-4 Diisostearate/Polyhydroxystearate/Sebacate) | 3.00 |
|   | 9041 Silicone Elastomer Blend (Dow Corning) (Dimethicone, Dimethicone Crosspolymer) | 5.00 |
|   | Cyclopentasiloxane | 6.40 |
|   | TEGOSOFT ® DEC (Diethylhexyl Carbonate) | 6.40 |
|   | Organic Polymer (Example 2) | 2.00 |

W/O emulsion

| Phase | Raw material | w/w-% |
|---|---|---|
|  | Hydrogenated Castor Oil | 0.10 |
|  | Paracera W 80 Wax (Paraffin, Microcristallina cera; Paramelt) | 0.10 |
| B | Aqua | ad 100 |
|  | Glycerin | 2.00 |
|  | Magnesium Sulfate Heptahydrate | 1.50 |
| C | Euxyl ® PE 9010 (Schülke & Mayr) (Phenoxyethanol, Ethylhexylglycerin) | 0.70 |

W/O Cream

| Phase | Raw material | w/w-% |
|---|---|---|
| A | ISOLAN ® PDI (Diisostearoyl Polyglyceryl-3 Dimer Dilinoleate) | 3.00 |
|  | Hydrogenated Castor Oil | 0.40 |
|  | Beeswax | 0.60 |
|  | TEGOSOFT ® CT (Caprylic/Capric Triglyceride) | 5.00 |
|  | TEGOSOFT ® P (Isopropyl Palmitate) | 5.00 |
|  | TEGOSOFT ® OER (Oleyl Erucate) | 4.00 |
|  | *Prunus Amygdalus Dulcis* (Sweet Almond) Oil | 5.00 |
|  | Organic Polymer (Example 3) | 3.00 |
| B | Aqua | ad 100 |
|  | Glycerin | 5.00 |
| C | Magnesium Sulfate Heptahydrate | 1.00 |
|  | Sodium Benzoate, Potassium Sorbate, Water (Euxyl K 712, Schülke & Mayr) | 0.50 |
|  | Citric Acid (10% in water) | q.s. |

Anhydrous stick

| Phase | Raw material | w/w-% |
|---|---|---|
| A | Organic Polymer (Example 1) | 10.00 |
|  | C12-15 Alkyl Benzoate | 30.00 |
|  | Isopropyl Palmitate | 15.00 |
|  | Octinoxate (Ethylhexyl Methoxycinnamate) | 7.50 |
|  | Octyldodecanol | 37.50 |

Anti-Aging Day Care

| Phase | Raw material | w/w-% |
|---|---|---|
| A | ABIL ® EM 90 (Cetyl PEG/PPG-10/1 Dimethicone Triglyceride) | 3.00 |
|  | TEGOSOFT ® AC (Isoamyl Cocoate) | 7.50 |
|  | TEGOSOFT ® DEC (Diethylhexyl Carbonate) | 7.00 |
|  | Organic Polymer (Example 2) | 2.50 |
|  | HyaCare ® Filler CL (Aqua, Ethylhexyl Stearate, Sodium Hyaluronate Crosspolymer, Polyglyceryl-4 Diisostearate/Polyhydroxystearate/Sebacate, Sodium Isostearate) | 2.50 |
|  | Tocopherol | 0.50 |
|  | Methyl Methacrylate Crosspolymer (Covabead LH 85, Sensient) | 2.00 |

Anti-Aging Day Care

| Phase | Raw material | w/w-% |
|---|---|---|
| B | Aqua | ad 100 |
|  | Sodium Chloride | 0.80 |
|  | Glycerin | 4.00 |
|  | Butylene Glycol | 4.00 |
|  | TEGO ® Pep 4-Even (Tetrapeptide-30; Glycerin) | 2.50 |
|  | Sodium Ascorbyl Palmitate | 1.50 |
|  | Urea | 2.50 |
|  | Sodium Bisulfite | 0.10 |
| Z | Preservative, Perfume | q.s. |

AP/Deo stick

| Phase | Raw material | w/w-% |
|---|---|---|
| A | PPG-14 Butyl Ether (Probutyl 14) | 13.20 |
|  | Hydrogenated Castor Oil (Castro Wax NF) | 4.50 |
|  | Cyclopentasiloxane (SF 1202) | 39.90 |
|  | C12-15 Alkyl Benzoate (Finsolve TN) | 5.30 |
|  | Fumed Silica (Aerosil 200) | 3.00 |
|  | Organic Polymer (Example 3) | 5.00 |
|  | Stearyl Alcohol (Lanette 18) | 6.00 |
|  | Aluminium Zirconium Tetrachlorohydrex Gly | 23.10 |

W/O emulsion

| Phase | Raw material | w/w-% |
|---|---|---|
| A | ABIL ® EM 90 (Cetyl PEG/PPG-10/1 Dimethicone) | 2.00 |
|  | TEGOSOFT ® OP (Ethylhexyl Palmitate) | 5.00 |
|  | TEGOSOFT ® CT (Caprylic/Capric Triglyceride) | 10.00 |
|  | TEGOSOFT ® DEC (Diethylhexyl Carbonate) | 10.00 |
|  | Organic Polymer (Example 3) | 1.00 |
|  | dermofeel ® viscolid (Hydrogenated Vegetable Oil) | 0.50 |
| B | Aqua | ad 100 |
|  | Sodium Chloride | 0.50 |
| C | Phenoxyethanol, Ethylhexylglycerin (euxyl ® PE 9010, Schülke & Mayr) | 0.80 |

Skin Replenishing Serum

| Phase | Raw material | w/w-% |
|---|---|---|
| A | TEGO ® Care 165 (Glyceryl Stearate; PEG-100 Stearate) | 3.00 |
|  | TEGO ® Alkanol 18 (Stearyl Alcohol) | 0.50 |

Skin Replenishing Serum

| Phase | Raw material | w/w-% |
|---|---|---|
| | Isononyl Isononanoate | 4.00 |
| | Hydrogenated Polyisobutene | 3.00 |
| | TEGOSOFT ® APM (PPG-3 Myristyl Ether) | 3.00 |
| | Organic Polymer (Example 3) | 0.50 |
| | Tocopherol | 0.50 |
| B | Aqua | ad 100 |
| | Butylene Glycol | 5.00 |
| | SKINMIMICS ® (Ceteareth-25; Glycerin; Cetyl Alcohol; Behenic Acid; Cholesterol; Ceramide NP; Ceramide NS; Ceramide EOS; Ceramide EOP; Ceramide AP; Caprooyl Phytosphingosine; Caprooyl Sphingosine) | 2.50 |
| C | Polyacrylamide; C13-14 Isoparaffin; Laureth-7 (Sepigel 305, Seppic) | 0.75 |
| Z | Preservative, Perfume | q.s. |

Dual-Action Wrinkle Serum

| Phase | Raw material | w/w-% |
|---|---|---|
| A | ABIL ® EM 97 S (Bis-PEG/PPG-14/14 Dimethicone; Dimethicone) | 1.00 |
| | ABIL ® EM 90 (Cetyl PEG/PPG-10/1 Dimethicone) | 1.50 |
| | Cyclopentasiloxane | 12.00 |
| | 9040 Silicone Elastomer Blend (Dow Corning) (Cyclopentasiloxane, Dimethicone Crosspolymer) | 3.00 |
| | TEGOSOFT ® DEC (Diethylhexyl Carbonate) | 3.00 |
| | Organic Polymer (Example 2) | 0.75 |
| | HyaCare ® Filler CL (Aqua; Ethylhexyl Stearate; Sodium Hyaluronate Crosspolymer; Polyglyceryl-4 Diisostearate/Polyhydroxystearate/Sebacate; Sodium Isostearate) | 2.50 |
| | Tocopherol | 0.50 |
| | Zinc Stearate | 0.50 |
| B | Aqua | ad 100 |
| | Sodium Chloride | 0.80 |
| | Glycerin | 4.00 |
| | Butylene Glycol | 4.00 |
| | TEGO ® Pep 4-17 (Tetrapeptide-21; Glycerin; Butylene Glycol; Aqua) | 0.50 |
| Z | Preservative, Perfume | q.s. |

Lip filler lipstick

| Phase | Raw material | w/w-% |
|---|---|---|
| A | TEGOSOFT ® G 20 (Octyldodecanol) | 15.00 |
| | TEGOSOFT ® CT (Caprylic/Capric Triglyceride) | 10.00 |
| | TEGOSOFT ® OER (Oleyl Erucate) | 2.00 |
| | TEGOSOFT ® MM (Myristyl Myristate) | 5.00 |
| | *Ricinus Communis* Seed Oil (Castor Oil, Aldrich) | 31.70 |
| | Olus Oil (Cremerlin ® PURA, Cremer Care) | 10.00 |
| | Stearyl Beeswax; Behenyl Beeswax (BW Ester BW67, Koster Keunen) | 5.00 |
| | Ozokerite (Kahlwax 1899, KahlWax) | 5.00 |
| | Cera Alba (Kahlwax 8104, KahlWax) | 4.00 |
| | *Euphorbia Cerifera* Wax (Kahlwax 2039L, KahlWax) | 2.00 |
| | Organic Polymer (Example 3) | 5.00 |
| B | Tocopherol | 0.10 |
| | Perfume | 0.20 |
| C | HyaCare ® Filler CL (Aqua; Ethylhexyl Stearate; Sodium Hyaluronate Crosspolymer; Polyglyceryl-4 Diisostearate/Polyhydroxystearate/Sebacate; Sodium Isostearate) | 5.00 |

W/O emulsion

| Phase | Raw material | w/w-% |
|---|---|---|
| A | Organic Polymer (Example 2) | 1.50 |
| | Cylcopentasiloxane; PEG/PPG-18/18 Dimethicone | 10.00 |
| | Cylcopentasiloxane | 16.00 |
| | C12-15 Alkyl Benzoate | 0.50 |
| B | Aqua | ad 100 |
| | Glycerin | 5.00 |
| | Sodium Chloride | 2.00 |
| C | Propylene Glycol; Diazolidinyl Urea; Methylparaben; Propylparaben | 0.50 |

O/W Sun Protect & Bronze

| Phase | Raw material | w/w-% |
|---|---|---|
| A | AXOL ® C 62 Pellets (Glyceryl Stearate Citrate) | 2.00 |
| | TEGO ® Alkanol 1618 (Cetearyl Alcohol) | 1.50 |
| | TEGOSOFT ® XC (Phenoxyethyl Caprylate) | 8.00 |
| | TEGOSOFT ® TN (C12-15 Alkyl Benzoate) | 4.00 |
| | Organic Polymer (Example 1) | 1.00 |
| | TEGO ® Sun T 805 (Titanium Dioxide, Trimethoxycaprylylsilane) | 1.50 |
| | Cyclomethicone | 3.00 |
| | Octocrylene | 9.00 |
| | Ethylhexyl Salicylate | 4.50 |
| | Butyl Methoxydibenzoylmethane | 2.00 |
| | Tocopheryl Acetate | 0.50 |
| | Xanthan Gum | 0.50 |
| B | Aqua | ad 100 |
| | Glycerin | 3.00 |
| | Panthenol | 1.00 |
| C | TEGO ® Carbomer 341 ER (Acrylates/C10-30 Alkyl Acrylate Crosspolymer) | 0.10 |
| | TEGOSOFT ® TN (C12-15 Alkyl Benzoate) | 0.40 |
| D | Sodium Hydroxide (10% in water) | q.s. |
| E | Butylene Glycol; Acetyl-L-Tyrosine; Hydrolyzed Vegetable Protein; Adenosin Triphosphate; Riboflavin (Unipertan VEG-2001) | 0.80 |
| Z | Preservative, Perfume | q.s. |

O/W Cream

| Phase | Raw material | w/w-% |
|---|---|---|
| A | TEGO ® Care PSC 3 (Polyglyceryl-3 Dicitrate/Stearate) | 3.00 |
| | TEGIN ® M Pellets (Glyceryl Stearate) | 0.90 |
| | TEGO ® Alkanol 18 (Stearyl Alcohol) | 0.60 |
| | TEGOSOFT ® P (Isopropyl Palmitate) | 7.00 |

O/W Cream

| Phase | Raw material | w/w-% |
|---|---|---|
| | *Prunus Amygdalus Dulcis* Oil | 5.00 |
| | TEGOSOFT ® CT (Caprylic/Capric Triglyceride) | 4.50 |
| | Triisostearin | 3.50 |
| | Organic Polymer (Example 1) | 1.5 |
| | Intelimer ® 13-1 (Poly C10-30 Alkyl Acrylate) | 1.5 |
| B | Aqua | ad 100 |
| | Glycerin | 3.00 |
| | Xanthan Gum (Keltrol CG-SFT, CP Kelco) | 0.30 |
| C | Sodium hydroxide (10% in water) | q.s. |
| Z | Preservative, Perfume | q.s. |

Lip filler color lipstick

| Phase | Raw material | w/w-% |
|---|---|---|
| A | *Ricinus Communis* Seed Oil; (Castor Oil, Aldrich) | 21.70 |
| | TEGOSOFT ® CT (Caprylic/Capric Triglyceride) | 20.00 |
| | Triisostearin | 10.00 |
| | TEGOSOFT ® OER (Oleyl Erucate) | 5.00 |
| | TEGOSOFT ® MM (Myristyl Myristate) | 7.50 |
| | *Euphorbia Cerifera* Wax (Kahlwax 2039L, KahlWax) | 6.00 |
| | *Copernicia Cerifera* Cera (Kahlwax 2442L, KahlWax) | 3.00 |
| | Ozokerite (Kahlwax 1899, KahlWax) | 4.00 |
| | Polyglyceryl-3 Beeswax (Cera Beilina, Koster Keunen) | 4.00 |
| | CI 15850 (Red no. 7), Hydrogenated Polydecene, Hydroxystearic Acid (Creasperse Bergonia, The Innovation Company) | 2.00 |
| B | Mica, CI 77491 (1:1) (Colorona Bordeaux, Merck) | 8.50 |
| | TEGO ® Feel C 10 (Cellulose) | 3.00 |
| C | Perfume | 0.30 |
| D | HyaCare ® Filler CL (Aqua; Ethylhexyl Stearate; Sodium Hyaluronate Crosspolymer; Polyglyceryl-4 Diisostearate/Polyhydroxystearate/Sebacate; Sodium Isostearate) | 5.00 |

After Shave Lotion

| Phase | Raw material | w/w-% |
|---|---|---|
| A | ABIL ® Care 85 (Bis-PEG/PPG-16/16 PEG/PPG-16/16 Dimethicone; Caprylic/Capric Triglyceride) | 1.50 |
| | TEGOSOFT ® CT (Caprylic/Capric Triglyceride) | 3.00 |
| | Cyclomethicone | 3.00 |
| | Organic Polymer (Example 2) | 0.50 |
| | Tocopheryl Acetate | 0.50 |
| | Menthyl Lactate (Frescolat ML) | 0.50 |
| B | TEGO ® SMO 80 V (Polysorbate 80) | 0.50 |
| | Aqua | ad 100 |
| | Glycerin | 2.00 |
| | Alcohol | 15.00 |
| C | TEGO ® Carbomer 141 (Carbomer) | 0.20 |
| | Xanthan Gum | 0.10 |
| | Mineral Oil (30 mPas) | 1.60 |
| D | Sodium hydroxide (10% in water) | q.s. |
| Z | Preservative, Perfume | q.s. |

W/O emulsion

| Phase | Raw material | w/w-% |
|---|---|---|
| A | Organic Polymer (Example 1) | 3.00 |
| | Isopropyl Palmitate | 4.00 |
| | Isopropyl Myristate | 4.00 |
| | Mineral Oil | 1.00 |
| | PEG-30 Dipolyhydroxystearate | 0.50 |
| | ABIL ® EM 97 (Bis-PEG/PPG-14/14 Dimethicone; Dimethicone) | 2.00 |
| | Cyclomethicone | 11.50 |
| B | Aqua | ad 100 |
| | Magnesium Sulfate | 0.50 |
| | Glycerin | 5.00 |
| C | Propylene Glycol; Diazolidinyl Urea; Methylparaben; Propylparaben | 1.00 |

W/O emulsion

| Phase | Raw material | w/w-% |
|---|---|---|
| A | ISOLAN ® GPS (Polyglyceryl-4 Diisostearate/Polyhydroxystearate/Sebacate) | 3.00 |
| | Cyclopentasiloxane | 6.40 |
| | TEGOSOFT ® DEC (Diethylhexyl Carbonate) | 6.40 |
| | Organic Polymer (Example 1) | 2.00 |
| | Dicaprylyl Carbonate, Stearalkonium Hectorite, Propylene Carbonate (Cosmedia ® Gel CC, Cognis) | 3.00 |
| B | Aqua | ad 100 |
| | Glycerin | 2.00 |
| | Magnesium Sulfate Heptahydrate | 1.50 |
| C | Phenoxyethanol, Ethylhexylglycerin (euxyl ® PE 9010, Schülke & Mayr) | 0.70 |

Retinol Cream

| Phase | Raw material | w/w-% |
|---|---|---|
| A | Isopropyl Palmitate | 10.00 |
| | *Simmondsia Chinensis* (Jojoba) Seed Oil | 1.00 |
| | Cyclotetrasiloxane | 5.00 |
| | Cetearyl Alcohol, Dicetyl Phosphate, Ceteth-10 Phosphate (Crodafos CES, Croda) | 5.00 |
| | PEG/PPG-18/18 Dimethicone | 2.50 |
| | *Prunus Armeniaca* (Apricot) Kernel Oil | 0.40 |
| | *Prunus Amygdalis Dulcis* (Sweet Almond) Oil | 0.60 |
| | Organic Polymer (Example 2) | 0.75 |
| | Intelimer ® 13-1 (Poly C10-30 Alkyl Acrylate) | 0.75 |
| B | Aqua | ad 100 |
| | Xanthan Gum | 0.75 |
| | Glycerin | 1.00 |
| C | InuMax Advanced Retinol (Aqua; Caprylic/Capric Triglyceride; Glycerin; Polysorbate 20; Retinol; Inulin Lauryl Carbamate; Behentrimonium Chloride; Sucrose Laurate; Disodium EDTA; Phenoxyethanol; Benzoic Acid; Dehydroacetic Acid; Ethylhexylglycerin | 3.75 |
| D | Preservative, Perfume | q.s. |

Anti-aging moisturizer

| Phase | Raw material | w/w-% |
|---|---|---|
| A | TEGO ® Care 450 (Polyglyceryl-3 Methylglucose Distearate) | 3.00 |
| | TEGIN ® M Pellets (Glyceryl Stearate) | 2.00 |
| | TEGO ® Alkanol 18 (Stearyl Alcohol) | 1.00 |
| | TEGOSOFT ® MM (Myristyl Myristate) | 1.00 |
| | TEGOSOFT ® DO (Decyl Oleate) | 8.00 |
| | TEGOSOFT ® OS (Ethylhexyl Stearate) | 9.00 |
| | Phytosphingosine SLC (Salicyloyl Phytosphingosine) | 0.10 |
| | Organic Polymer (Example 2) | 1.25 |
| | Organic Polymer (Example 3) | 1.25 |

Anti-aging moisturizer

| Phase | Raw material | w/w-% |
|---|---|---|
| B | Glycerin | 3.00 |
|  | Aqua | ad 100 |
| C | TEGO ® Carbomer 134 (Carbomer) | 0.20 |
|  | TEGOSOFT ® P (Isopropyl Palmitate) | 0.80 |
| D | Sodium hydroxide (10% in water) | q.s. |
| Z | Preservative, Perfume | q.s. |

Sun Care Foam SPF 50

| Phase | Raw material | w/w-% |
|---|---|---|
| A | TEGO ® Care PBS 6 (Polyglyceryl-6 Stearate (and) Polyglyceryl-6 Behenate) | 3.00 |
|  | TEGOSOFT ® TN (C12-15 Alkyl Benzoate) | 5.00 |
|  | Organic Polymer (Example 1) | 0.50 |
|  | Bis-Ethylhexyloxyphenol Methoxyphenyl Triazine | 4.50 |
|  | Butyl Methoxydibenzoylmethane | 3.00 |
|  | Octocrylene | 8.00 |
|  | Homomethyl Salicylate | 6.00 |
|  | Ethylhexyl Salicylate | 2.50 |
|  | TEGO ® Feel C 10 (Cellulose) | 2.00 |
| B | Aqua | ad 100 |
|  | Glycerin | 2.00 |
|  | EDTA Disodium | 0.05 |
| C | TEGOSOFT ® TN (C12-15 Alkyl Benzoate) | 0.80 |
|  | TEGO ® Carbomer 141 (Carbomer) | 0.20 |
|  | Xanthan Gum (Keltrol CG-SFT, CP Kelco) | 0.20 |
| D | Aqua | 11.68 |
|  | Phenylbenzimidazole Sulfonic Acid | 3.00 |
|  | Trometamine | 1.32 |
| E | Phenoxyethanol, Ethylhexylglycerin (Euxyl PE 9010, Schülke & Mayr GmbH) | 0.70 |
|  | TEGO ® Betain 810 (Capryl/Capramidopropyl Betaine) | 1.00 |
|  | REWOTERIC ® AM C (Sodium Cocoamphoacetate) | 1.00 |
| F | Trometamine (30% in water) | q.s. |

Shaving Cream

| Phase | Raw material | w/w-% |
|---|---|---|
| A | Stearic Acid | 18.00 |
|  | Mineral Oil | 5.00 |
|  | Polysorbate 60 | 5.00 |
|  | Organic Polymer (Example 3) | 1.00 |
|  | Dow Corning 200 Fluid 1000 cSt | 1.00 |
| B | Aqua | ad 100 |
|  | Glycerin | 5.00 |
|  | DMDM Hydantoin | 0.50 |
|  | Triethanolamin | 0.06 |

PEG-free AP/Deo Lotion

| Phase | Raw material | w/w-% |
|---|---|---|
| A | TEGO ® Care PS (Methyl Glucose Sesquistearate) | 1.75 |
|  | TEGO ® Care PL 4 (Polyglyceryl-4 Laurate) | 0.25 |
|  | TEGOSOFT ® DEC (Diethylhexyl Carbonate) | 3.50 |
|  | TEGOSOFT ® PBE (PPG-14 Butyl Ether) | 3.50 |
|  | Organic Polymer (Example 2) | 2.50 |
|  | TEGO ® Cosmo P 813 (Polyglyceryl-3 Caprylate) | 0.50 |
| B | Aqua | ad 100 |
|  | Hydroxyethyl Cellulose (Natrosol 250 HHR, Aqualon) | 1.00 |
| C | Aluminium Chlorohydrate (Reach 501 L, Reheis) | 15.00 |
| D | Perfume | 1.00 |
| Z | Preservative | q.s. |

W/O Sun Protection Shake-Shake

| Phase | Raw material | w/w-% |
|---|---|---|
| A | ABIL ® EM 90 (Cetyl PEG/PPG-10/1 Dimethicone) | 1.00 |
|  | TEGOSOFT ® XC (Phenoxyethyl Caprylate) | 11.00 |
|  | TEGOSOFT ® DEC (Diethylhexyl Carbonate) | 2.50 |
|  | Cyclomethicone | 12.00 |
|  | Octocrylene | 6.00 |
|  | Ethylhexyl Salicylate | 2.00 |
|  | Butyl Methoxydibenzoylmethane | 0.80 |
|  | Bis-Ethylhexyloxyphenol Methoxyphenyl Triazine (Tinosorb S, BASF SE) | 1.50 |
|  | TEGO ® Sun T 805 (Titanium Dioxide, Trimethoxycaprylylsilane) | 2.00 |
|  | VP/Hexadecene Copolymer (Antarone V-216, Ashland) | 0.50 |
|  | Organic Polymer (Example 3) | 0.50 |
| B | Aqua | 4.43 |
|  | Phenylbenzimidazole Sulfonic Acid (Eusolex 232, Merck KGaA) | 0.50 |
|  | Sodium Hydroxide | 0.07 |
| C | Distarch Phosphate (MAIS PO4 PH "B", Agrana Stärke GmbH) | 1.50 |
|  | Alcohol | 1.00 |
|  | Glycerin | 6.00 |
|  | Aqua | ad 100 |
|  | Preservative, Perfume | q.s. |

The invention claimed is:

1. A polymer, comprising: monomeric units of general formula (I)

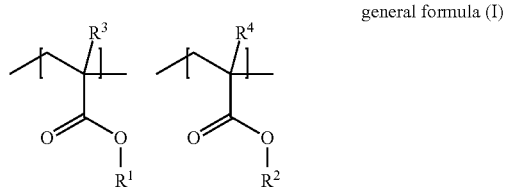

general formula (I)

wherein $R^1$=independently from each other selected from the group consisting of alkyl radicals and alkenyl radicals, which both may be branched or straight chained, unsubstituted or substituted, $R^2$=independently from each other selected from the group consisting of hydroxyl substituted hydrocarbyl radicals, $R^3$ and $R^4$ independently from each other selected from the group consisting of H and methyl, and with the monomeric units of general formula (I) making up at least 90 wt.-%, of the total weight of the polymer, with at least 90 wt.-% of all $R^1$ are selected from the group of alkyl and alkenyl radicals with from 6 to 32, carbon atoms, with the wt.-% referring to the sum of all $R^1$ present in the polymer, and with the weight ratio of the sum of all $R^2$-bearing-units to the sum of all $R^1$-bearing-units being in the range of from 1:100 to 1:0.5, wherein the polymer has a number average molecular weight $M_n$ in the range of from 2,000 to 8,100 g/mol, wherein the polymer has a weight average molecular weight $M_w$ in the range of from 12,000 to 250,000 g/mol, and wherein the $M_n$ and $M_w$ are selected such that the polymer has a ratio of weight average molecular weight $M_w$ to number average molecular weight $M_n$ in the range of from 0.1 to 3.6.

2. The polymer according to claim 1, wherein the polymer has a melting point in the range of from 41° C. to 69° C.

3. The polymer of claim 1, wherein the polymer has a ratio of weight average molecular weight $M_w$ to number average molecular weight $M_n$ in the range of from 2.3 to 3.3.

4. The polymer of claim 1, wherein
$R^1$=independently from each other selected from the group consisting of stearyl and behenyl,
$R^2$=2-Hydroxyethyl, and
$R^3$ and $R^4$=H.

5. A process for preparing a polymer of claim 1, comprising:
A) providing a monomer (1) of general formula (II) and a monomer (2) of general formula (III)

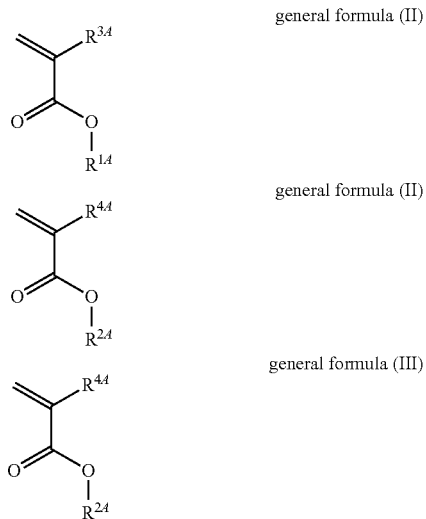

with
$R^{1A}$=independently from each other selected from the group consisting of alkyl radicals and alkenyl radicals, which both may be branched or straight chained, unsubstituted or substituted, $R^{2A}$=independently from each other selected from the group consisting of hydroxyl substituted hydrocarbyl radicals,
$R^{3A}$ and $R^{4A}$=independently from each other selected from the group consisting of H and methyl, and
with
at least 90 wt.-% of all $R^{1A}$ are selected from the group of alkyl and alkenyl radicals with from 6 to 32, carbon atoms, with the wt.-% referring to the sum of all $R^{1A}$ present in the polymer, and a weight ratio of monomer (1) to monomer (2) in the range of from 1:100 to 1:0.5,
B) addition of at least one initiator to polymerize the monomers and performing a radical polymerization, optionally
C) removal of excess of monomers, and, optionally,
D) purification of the obtained polymer, wherein the initiator is added in an amount of from 5 to 20,000 ppm, wherein the ppm refers to the total weight of the sum of all monomers (1) and (2) provided in process step A).

6. The process according to claim 5, wherein the initiator is selected from the group consisting of 2,2'-azo-bis(2-methyl propionitrile), 2,2'-azodi(2-methylbutyronitrile), 1,1'-azodi(hexahydrobenzonitrile), 4,4'-azo-bis(4-cyanovaleric acid), 2,2'-azo-bis(2,4-dimethyl valeronitrile), and 2,2'-azo-bis(2-cyclopropyl propionitrile), 2,2'-azo-bis(2-cyclobutyl propionitrile), 2,2'-azo-bis(2-cyclobutyl propionitrile), 2,2'-azo-bis(2,4-dimethyl valeronitrile), 1,1'-azo-bis(1-cycloheptanenitrile), 2,2'-azo-bis(methylheptylonitrile), 2,2'-azo-bis(2-cyclohexyl propionitrile), azo-bisisobutyramidine 2HCl, phenyl-azo-triphenylmethane, 4-hydroxyphenyl-azo-triphenylmethane, peroxide and peroxy compounds, such as benzoyl peroxide, tert-butyl peroxy pivalate, tert-amyl peroxypivalate, acetyl peroxide, propionyl peroxide, 2-isopropionyl peroxide, butyryl peroxide, diisobutyryl peroxide, dilauroyl peroxide, didecanoyl peroxide, cumyl peroxyneodecanoate, 1,1,3,3-tetramethylbutyl peroxyneodecanoate, tert-butyl peroxydiethylacetate, tert-amyl peroxy-2-ethylhexanoate, tertamyl peroxy-2-ethylhexanoate, 2-methoxybenzoyl peroxide, cumyl peroxyneoheptanoate, tert-amyl peroxyneodecanoate, tert-butyl peroxyneodecanoate, tert-butyl peroxyneoheptanoate, tert-amyl peroxyacetate, 4-benzylidenebutyryl peroxide, methyl phtholoyl peroxide, 1,1-di(tert-amylperoxy)cyclohexane, 3,6,9-triethyl-3,6,9-trimethyl-1,4,7-triperoxonane, isopropylcumyl hydroperoxide, 1,1,3,3-tetramethylbutyl hydroperoxide, cumyl hydroperoxide, tert-butyl hydroperoxide, tert-amyl hydroperoxide, diethyl peroxydicarbonate, tert-butylperoxy isopropyl carbonate, tert-butylperoxy 2-ethylhexyl carbonate, di-sec-butyl peroxydicarbonate, diisopropyl peroxydicarbonate, di(4-tert-butylcyclohexyl) peroxydicarbonate, di(2-ethylhexyl) peroxydicarbonate, dicetyl peroxydicarbonate, dimyristyl peroxydicarbonate, tert-amylperoxy 2-ethylhexyl carbonate, tert-butylperoxy isopropyl carbonate, tertbutyl peroxy 2-ethylhexyl carbonate, ethyltert-butyl peroxalate, benzyl (tert-butyl peroxy) oxalate, tertiary-butyl-N-(3-tolylperoxy) carbamate, potassium persulfate and mixtures thereof.

7. The process according to claim 5, wherein in step B) at least one chain transfer agent is present, in an amount such that the weight ratio of added initiator and chain transfer agent is in the range of from 1:20 to 1:0.1.

8. The process according to claim 7, wherein the chain transfer agent is selected from the group consisting of tetrachloromethane, bromotrichloromethane, isooctyl 3-mercaptopropionate, 4-methylbenzenethiol, tert-nonyl mercaptan, pentaerythritol tetrakis(2-mercaptoacetate), pentaerythritol tetrakis(3-mercaptopropionate), 4,4'-thiobisbenzenethiol, trimethylolpropane tris(3-mercaptopropionate), 1,8-dimercapto-3,6-dioxaoctane, n-dodecanethiol, ethyl mercaptan, mercaptoethanol, mercaptopropanol, mercaptobutanol, mercaptohexanol, mercaptooctanol, propanethiol, dithiothreitol, cysteine, homocysteine, glutathione, tertdodecanethiol, thioglycolic acid, dimercaptosuccinic, 2,3-dimercapto-1-propanesulfonic acid, acetylcysteine and thiophenol.

9. The process according to claim 5, wherein no chain transfer agent is present in the process.

10. The polymer obtained by the process of claim 5.

11. A personal care formulation containing the polymer of claim 1.

12. A film comprising the polymer of claim 1.

13. A fragrance comprising the polymer of claim 1.

14. An emulsion comprising the polymer of claim 1.

15. A dispersion for solid pigments comprising the polymer of claim 1.

16. The polymer according to claim 1, wherein
$R^1$=independently from each other selected from the group consisting of alkyl radicals and alkenyl radicals, which both may be branched or straight chained substituted by hydroxyl-groups, $R^2$=independently from each other selected from the group consisting of alkyl radicals with from 1 to 10 carbon atoms, $R^3$ and $R^4$=H, and with the monomeric units of general formula (I) making up for at least 95 wt.-% of the total weight of the polymer, with at least 90 wt.-% of all $R^1$ are selected from the group of alkyl and alkenyl radicals with from 10 to 26 carbon atoms, with the wt.-% referring to the sum of all $R^1$ present in the polymer, and with the weight ratio of the sum of all $R^2$-bearing-units to the sum of all $R^1$-bearing-units being in the range of from 1:60 to 1:0.8, wherein the polymer has a number average molecular weight $M_n$ in the range of from 5,000 to 8,500 g/mol.

17. The polymer according to claim 1, wherein $R^1$=independently from each other selected from the group consisting of alkyl radicals and alkenyl radicals, which both may be branched or straight chained substituted by hydroxyl-groups, $R^2$=independently from each other selected from the group consisting of alkyl radicals with from 2 to 6 carbon atoms, $R^3$ and $R^4$=H, and with the monomeric units of general formula (I) making up for at least 95 wt.-% of the total weight of the polymer, with at least 90 wt.-% of all $R^1$ are selected from the group of alkyl and alkenyl radicals with 12 to 22 carbon atoms, with the wt.-% referring to the sum of all $R^1$ present in the polymer, and with the weight ratio of the sum of all $R^2$-bearing-units to the sum of all $R^1$-bearing-units being in the range of 1:30 to 1:1.1, wherein the polymer has a number average molecular weight $M_n$ in the range of from 7,000 to 8,000 g/mol.

18. The polymer according to claim 1, wherein the polymer has a melting point in the range of 62° C. to 67° C.

19. The polymer of claim 2, wherein $R^1$=independently from each other selected from the group consisting of stearyl and behenyl, $R^2$=2-hydroxyethyl, $R^3$ and $R^4$=H.

* * * * *